US011926875B2

(12) United States Patent
Tripathi et al.

(10) Patent No.: US 11,926,875 B2
(45) Date of Patent: Mar. 12, 2024

(54) METHOD FOR DETECTING PRESENCE OR ABSENCE OF CANCER IN A SUBJECT USING MESSENGER RNA BIOMARKERS

(71) Applicant: 23IKIGAI PTE LTD, Singapore (SG)

(72) Inventors: Vinay Kumar Tripathi, Thane (IN); Ashish Tripathi, Thane (IN)

(73) Assignee: 23IKIGAI PTE LTD, Singapore (SG)

(*) Notice: Subject to any disclaimer, the term of this patent is extended or adjusted under 35 U.S.C. 154(b) by 0 days.

(21) Appl. No.: 16/993,226

(22) Filed: Aug. 13, 2020

(65) Prior Publication Data

US 2020/0370134 A1    Nov. 26, 2020

Related U.S. Application Data

(63) Continuation of application No. PCT/IN2019/050453, filed on Jun. 13, 2019.

(30) Foreign Application Priority Data

Jun. 13, 2018  (IN) .............................. 201821022052
Dec. 10, 2018  (IN) .............................. 201821046670

(51) Int. Cl.
| C12Q 1/6886 | (2018.01) |
| C07K 14/47 | (2006.01) |
| C12N 5/0735 | (2010.01) |
| C12N 5/0797 | (2010.01) |
| C12Q 1/6806 | (2018.01) |

(52) U.S. Cl.
CPC ........ *C12Q 1/6886* (2013.01); *C07K 14/4705* (2013.01); *C12N 5/0623* (2013.01); *C12Q 1/6806* (2013.01); *C12N 5/0606* (2013.01); *C12Q 2600/106* (2013.01); *C12Q 2600/112* (2013.01); *C12Q 2600/158* (2013.01)

(58) Field of Classification Search
CPC ............... C12Q 1/6886; C12Q 1/6806; C12Q 2600/106; C12Q 2600/112; C12Q 2600/158; C12N 5/0606; C12N 5/0623; C07K 14/4705
USPC .................................. 435/2, 6.12, 6.14, 7.21
See application file for complete search history.

(56) References Cited

FOREIGN PATENT DOCUMENTS

JP    2010178650 A    *   8/2010

OTHER PUBLICATIONS

Di et al., "The stem cell markers Oct4A, Nanog and c-Myc are expressed in ascites cells and tumor tissue of ovarian cancer patients", 2013, Cell Oncology 36, p. 363-374.*
Pierini et al., "Effi cient isolation and enrichment of mesenchymal stem cells from bone marrow", 2012, Cytotherapy 14, p. 686-693.*
Density Gradient Centrifugation Protocol, "Isolation and Cryopreservation of PBMCs—Ficoll Method without plasma collection", 2007, p. 1-11, https://www.immunetolerance.org/sites/default/files/Separation%20of%20mononuclear%20cells%20from%20whole%20blood%20using%20Ficoll%20gradients.pdf, [accessed May 27, 2021].*
Vissers et al. (1988) J. Immunol. Meth., vol. 110, 203-207.*
Tripathi et al. (2021) Stem Cell Rev. and Rep., vol. 17, 1827-1839.*
Bhartiya et al. (2012) Stem Cells and Development, vol. 21(1), 1-6.*
Zhang et al. (2012) Stem Cell Rev and Rep, vol. 8, 917-925.*
Ratajczak et al. (2009) Am. J. Pathol., vol. 174(6), 1-8.*
Sovalat et al. (2016) Stem Cells International, vol. 2016, Article ID 7651645, doi.org/10.1155/2016/7651645, pp. 1-8.*
Abbott (2013) Nature, vol. 499, p. 390.*
International Search Report and Written Opinion for Application No. PCT/IN2019/050453, dated Sep. 13, 2019.
Mansoori et al., "Circulating cancer stem sell markers in breast carcinomas: a systematic review protocol", Systematic Reviews, Biomed Central Ltd., 22:1444-1452 (2015).
Mirzaei et al., "Upregulation of circulating cancer stem cell marker, DCLK1 but not Lgr5, in chemoradiotherapy-treated colorectal cancer patients", Tumor Biology. 36:4801-4810 (2015).
Rhee et al., "Simultaneous detection of mRNA and protein stem cell markers in live cells", BMC Biotechnology, Biomed Central Ltd. 9:30 (2009).
Hong et al., "Increased Expression of Circulating Cancer Step Cell Markers During the Perioperative Period Predicts Early Recurrence After Curative Resection of Hepatocellular Carcinoma", Annals of Surgical Oncology. 22:1444-1452 (2015).
Scatena et al., "Circulating tumour cells and cancer stem cells: A role for proteomics in defining the interrelationships between function, phenotype and differentiation with potential clinical applications", BBA—Reviews on Cancer. 1834:129-143 (2013).

* cited by examiner

*Primary Examiner* — Anne Marie S Wehbe
(74) *Attorney, Agent, or Firm* — Wilson Sonsini Goodrich & Rosati

(57) ABSTRACT

The present disclosure discloses an in-vitro method for detecting presence of metabolically altered cells. Also, an in-vitro method for detecting presence of quiescent cells has been disclosed. The present disclosure discloses an in-vitro method for detecting and predicting presence of cancer. The present disclosure discloses an in-vitro method for monitoring response to anti-cancer therapy. The present disclosure analyses expression of at least one biomarker of pluripotent stem cell for detecting or predicting or monitoring cancer. A related use of the at least one biomarker of pluripotent stem cell marker along with a method of treatment comprising the in-vitro method of detection or prediction has been disclosed herewith.

18 Claims, 14 Drawing Sheets

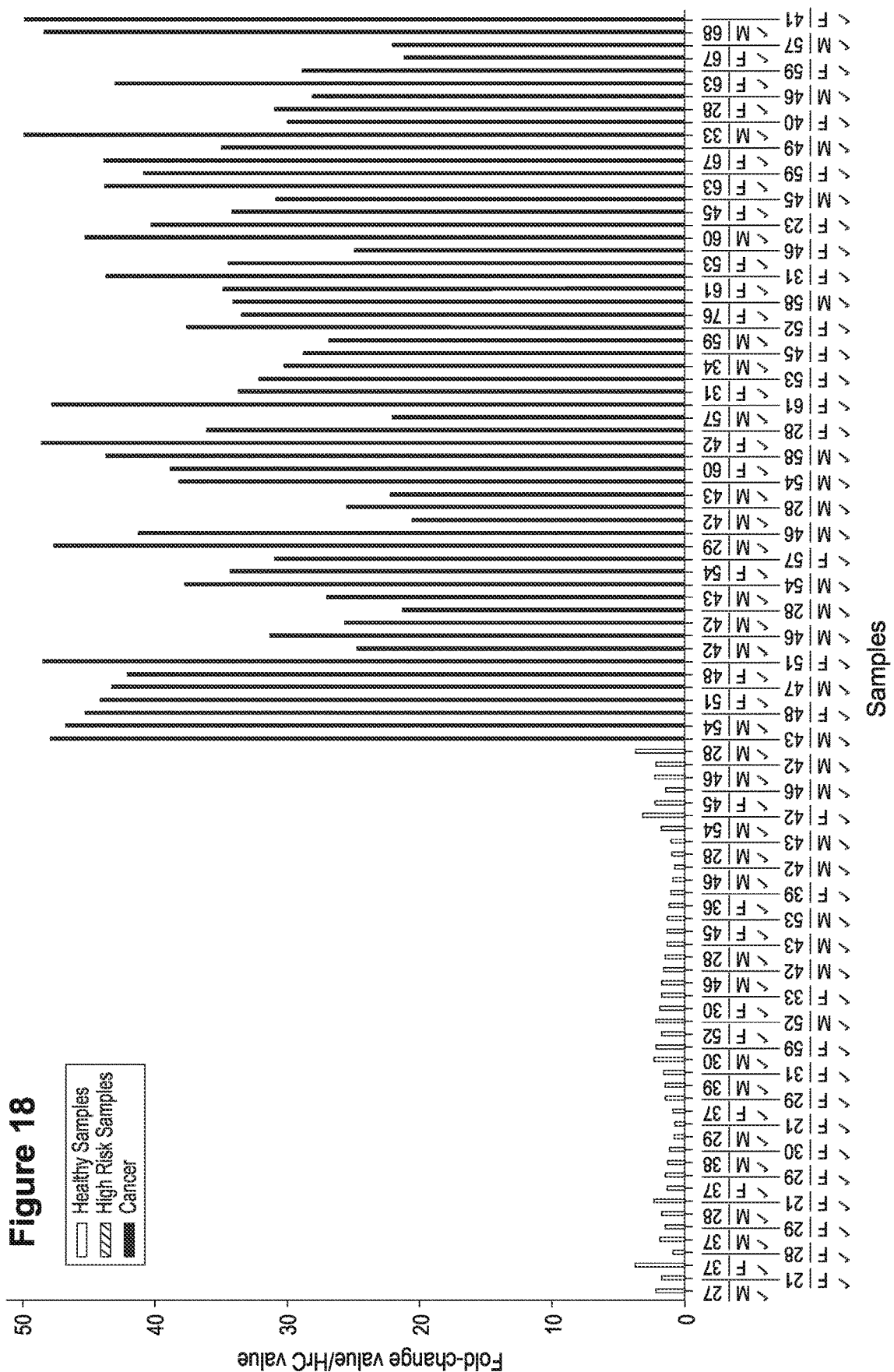

METHOD FOR DETECTING PRESENCE OR ABSENCE OF CANCER IN A SUBJECT USING MESSENGER RNA BIOMARKERS

CROSS REFERENCE

This application is a continuation of International Application No. PCT/IN2019/050453, filed Jun. 13, 2019, which claims the benefit of IN Application No. 201821022052, filed Jun. 13, 2018, and IN Application No. 201821046670, filed Dec. 10,2018, each of which is incorporated by reference herein in its entirety.

FIELD OF INVENTION

The present disclosure broadly relates to the field of pluripotent stem cell biomarkers, and particularly provides an in-vitro method for detecting and predicting cancer by using the pluripotent stem cell biomarkers in a blood sample.

BACKGROUND OF INVENTION

Cancer is a major health concern worldwide, accounting for millions of deaths. It has been reported that around 11 million people per year are diagnosed as patients carrying tumours worldwide, and it is speculated that this number will increase to more than 16 million by the year 2020 (Ferlay et al. International journal of cancer 136.5 E359-E386. 2015). The biologic heterogeneity of this disease and the vast populations afflicted by it, pose the pivotal questions of when and whom to treat and with which therapies. These important questions can only be addressed through the development of more accurate and informative biomarkers.

The treatment for cancer very much depends on the stage at which the disease is diagnosed. With the technological improvements happening at a global level, chances of treating cancer have been increased in the last few decades. The check point is the stage at which the diseases are detected. There are certain occasions where the cancer cannot be treated if it is detected at an advanced stage. The chances of a successful treatment increase if the cancer is diagnosed at a very early stage. The method of detection plays a vital role in this aspect and the use of specific biomarkers is an active field of research.

The non-specific nature of cancer symptoms makes diagnosis difficult. In certain cases, the patient remains asymptotic. Therefore, early signs and symptoms of cancer are often neglected by the patient which provides an opportunity for the cancer to spread in the absence of any medical intervention. By the time the patient seeks medical help, the cancer may be out of reach of available clinical treatments. Moreover, unavailability of good biomarkers is another hindrance for cancer treatment.

Cancer can be detected by several ways, including the medical imaging, tissue biopsy, and liquid biopsy. Once a possible cancer is detected it is usually diagnosed by microscopic examination of a tissue sample from a tissue biopsy. Detecting and diagnosing cancers early on is essential when it comes to treatment outcome and survival, especially when it comes to highly malignant tumors. From several decades, the only method for detecting cancer in humans has been to remove surgically a little portion of the tumour and to examine it with a microscope to look for cancer cells in the tissue. Unfortunately, this surgical intervention can only be carried out when the tumour has attained a certain volume or begins to be the cause of functional disorders. As this method can be used only when clinical symptoms are present, it cannot be considered as the best one for an early diagnosis of cancer or, in other words, it cannot be used as a screening test routinely made before any clinical sign of cancer. Therefore, there is a need to develop a simple yet highly sensitive and specific cancer detection systems and methods to overcome the above and other problems.

Biomarkers are not only important for diagnostic purposes but can also be of great prognostic value. With the identification of the right biomarker, the cancer progression and effect and success of chemotherapeutic drugs can be evaluated in great details. There is an urgent need to identify reliable biomarkers for different cancers and also to develop methods for efficient detection and prediction of cancer and/or metabolically altered and/or quiescent cells.

SUMMARY OF INVENTION

In an aspect of the present disclosure, there is provided an in-vitro method for detecting presence of metabolically altered cells, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects the presence of metabolically altered cells.

In a second aspect of the present disclosure, there is provided an in-vitro method for detecting presence of quiescent cells, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects the presence of quiescent cells.

In a third aspect of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer.

In a fourth aspect of the present disclosure, there is provided an in-vitro method for predicting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample predicts cancer.

In a fifth aspect of the present disclosure, there is provided an in-vitro method for monitoring response to cancer treatment, said method comprising: (a) obtaining a blood sample at a time point during an anti-cancer therapy; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference sample to monitor the response to cancer treatment.

In a sixth aspect of the present disclosure, there is provided an in-vitro method for detecting a positive response to cancer treatment, said method comprising: (a) obtaining a blood sample-I, before administration of an anti-cancer therapy; (b) obtaining a blood sample-II, after administration of the anti-cancer therapy; (c) enriching pluripotent stem cells from the blood sample-I to obtain a mixture-I comprising said pluripotent stem cells; (d) enriching pluripotent stem cells from the blood sample-II to obtain a mixture-II comprising said pluripotent stem cells; (e) obtaining nucleic acid-I from the mixture-I; (f) obtaining nucleic acid-II from the mixture-II; (g) independently performing an assay with the nucleic acid-I and the nucleic acid-II for analysing expression level of at least one biomarker of pluripotent stem cell; and (h) comparing the expression levels of the at least one biomarker of pluripotent stem cell from the nucleic acid-II with the expression level of the at least one biomarker of pluripotent stem cell from the nucleic acid-I, wherein a decrease in the expression level of the at least one biomarker of pluripotent stem cell from the nucleic acid-II as compared to the expression level of the at least one biomarker of pluripotent stem cell from the nucleic acid-I detects a positive response to the cancer treatment.

In a seventh aspect of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed.

In an eighth aspect of the present disclosure, there is provided a use of a pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for detecting cancer from a blood sample.

In a ninth aspect of the present disclosure, there is provided a use of a pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for predicting cancer from a blood sample.

In a tenth aspect of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for grading stage of cancer from a blood sample.

In an eleventh aspect of the present disclosure, there is provided a use of a pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for monitoring progression of anti-cancer therapy from a blood sample.

In a twelfth aspect of the present disclosure, there is provided a method for treating cancer, said method comprising: (a) obtaining a blood sample from a subject; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer; and (f) administering an anti-cancer therapy to the subject for treating cancer.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF ACCOMPANYING DRAWINGS

The following drawings form a part of the present specification and are included to further illustrate aspects of the present disclosure. The disclosure may be better understood by reference to the drawings in combination with the detailed description of the specific embodiments presented herein.

Figure 10:
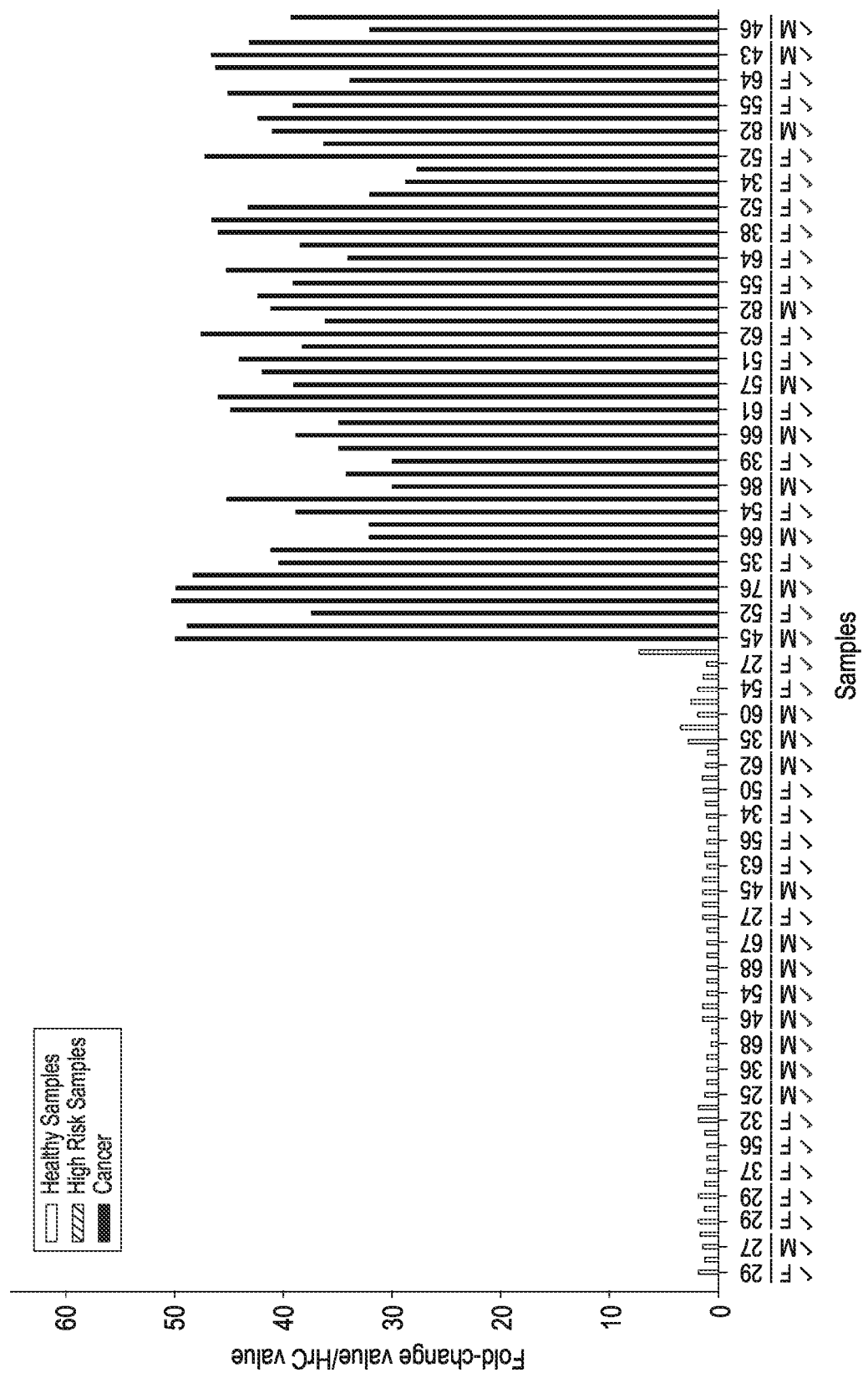

FIG. 10 a representative second graph showing the fold-change value for at least one biomarker of pluripotent stem cell as disclosed in the present study with a cohort of 1000 samples, in accordance with an embodiment of the present disclosure. The tick marks below show concurrence with the actual clinical status by an independent reviewer in the blinded study.

Figure 11:
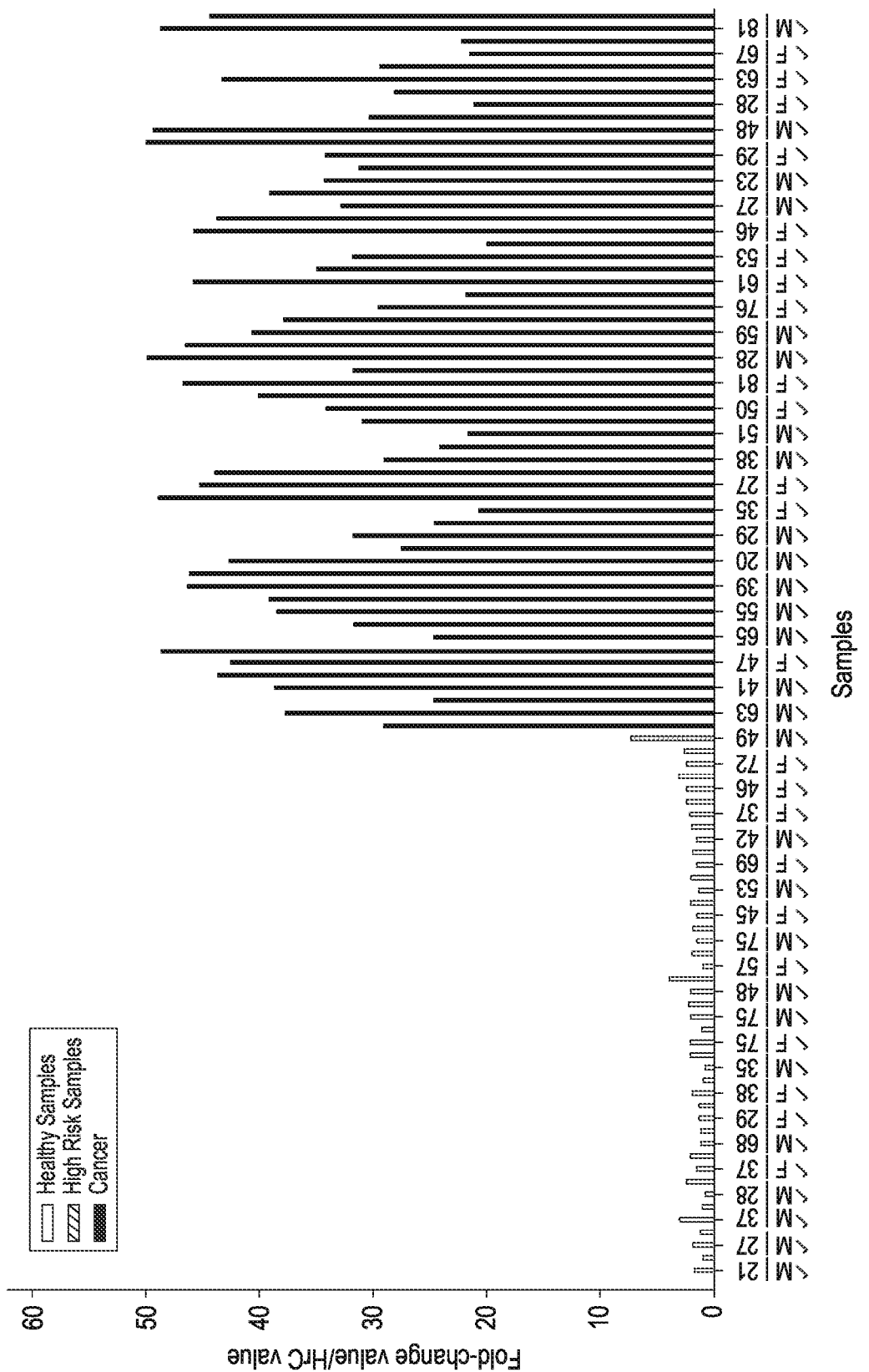

FIG. 11 depicts a representative third graph showing the fold-change value for at least one biomarker of pluripotent stem cell as disclosed in the present study with a cohort of 1000 samples study, in accordance with an embodiment of the present disclosure. The tick marks below show concurrence with the actual clinical status by an independent reviewer in the blinded study.

Figure 12:
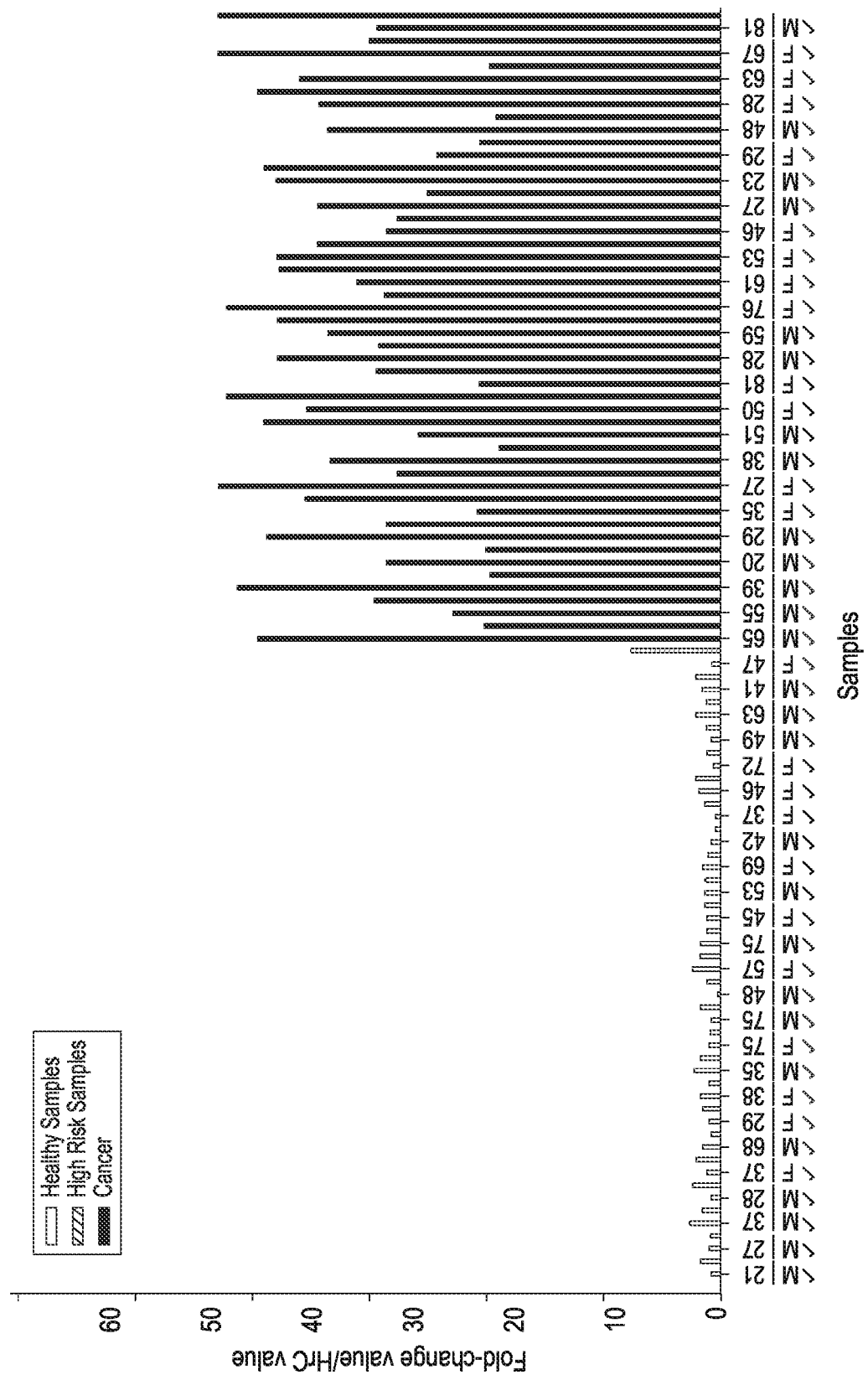

FIG. 12 depicts a representative fourth graph showing the fold-change value for at least one biomarker of pluripotent stem cell as disclosed in the present study with a cohort of 1000 samples study, in accordance with an embodiment of the present disclosure. The tick marks below show concurrence with the actual clinical status by an independent reviewer in the blinded study.

Figure 13:
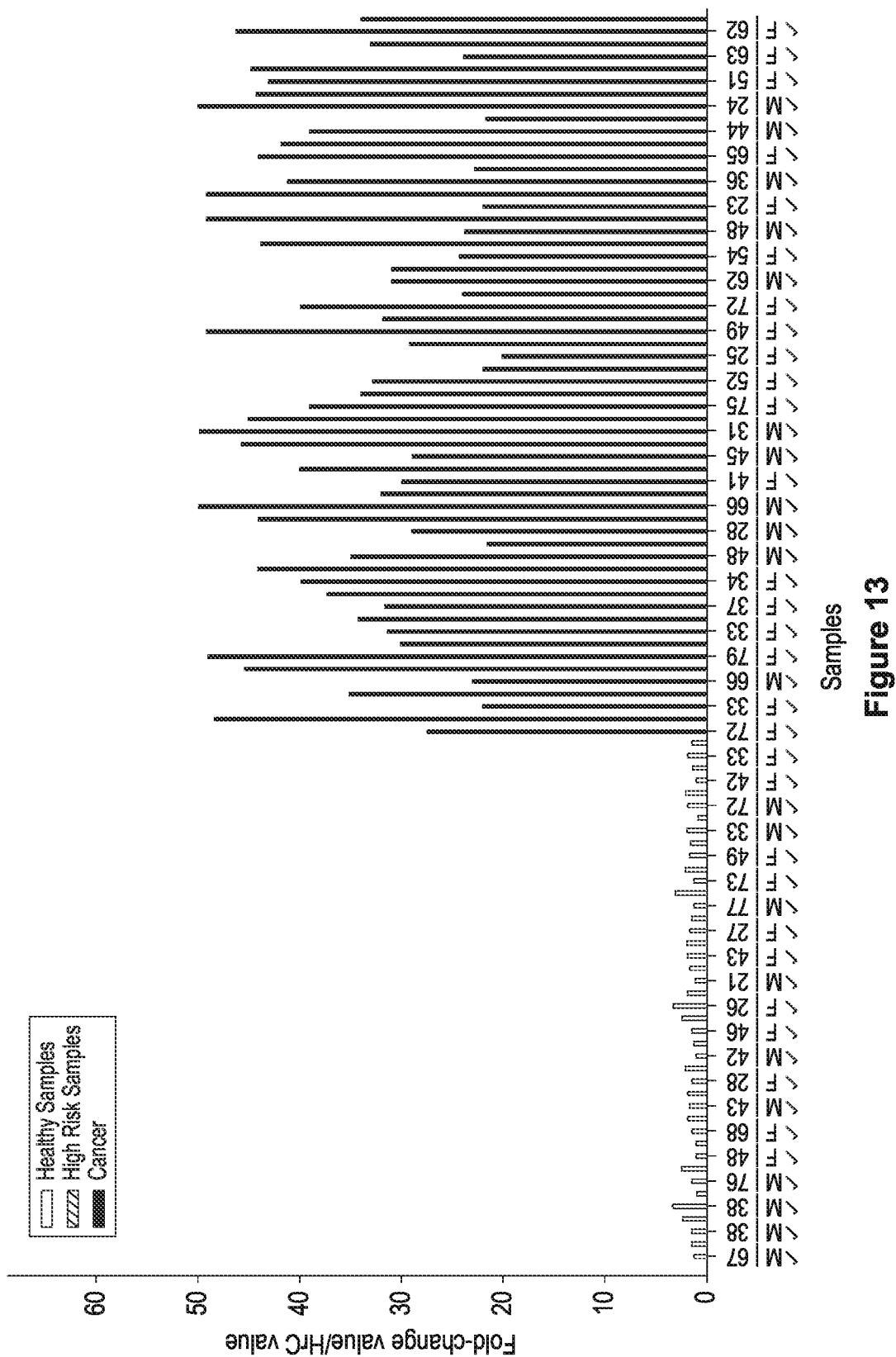

FIG. 13 depicts a representative fifth graph showing the fold-change value for at least one biomarker of pluripotent stem cell as disclosed in the present study with a cohort of 1000 samples, in accordance with an embodiment of the present disclosure. The tick marks below show concurrence with the actual clinical status by an independent reviewer in the blinded study.

Figure 14:
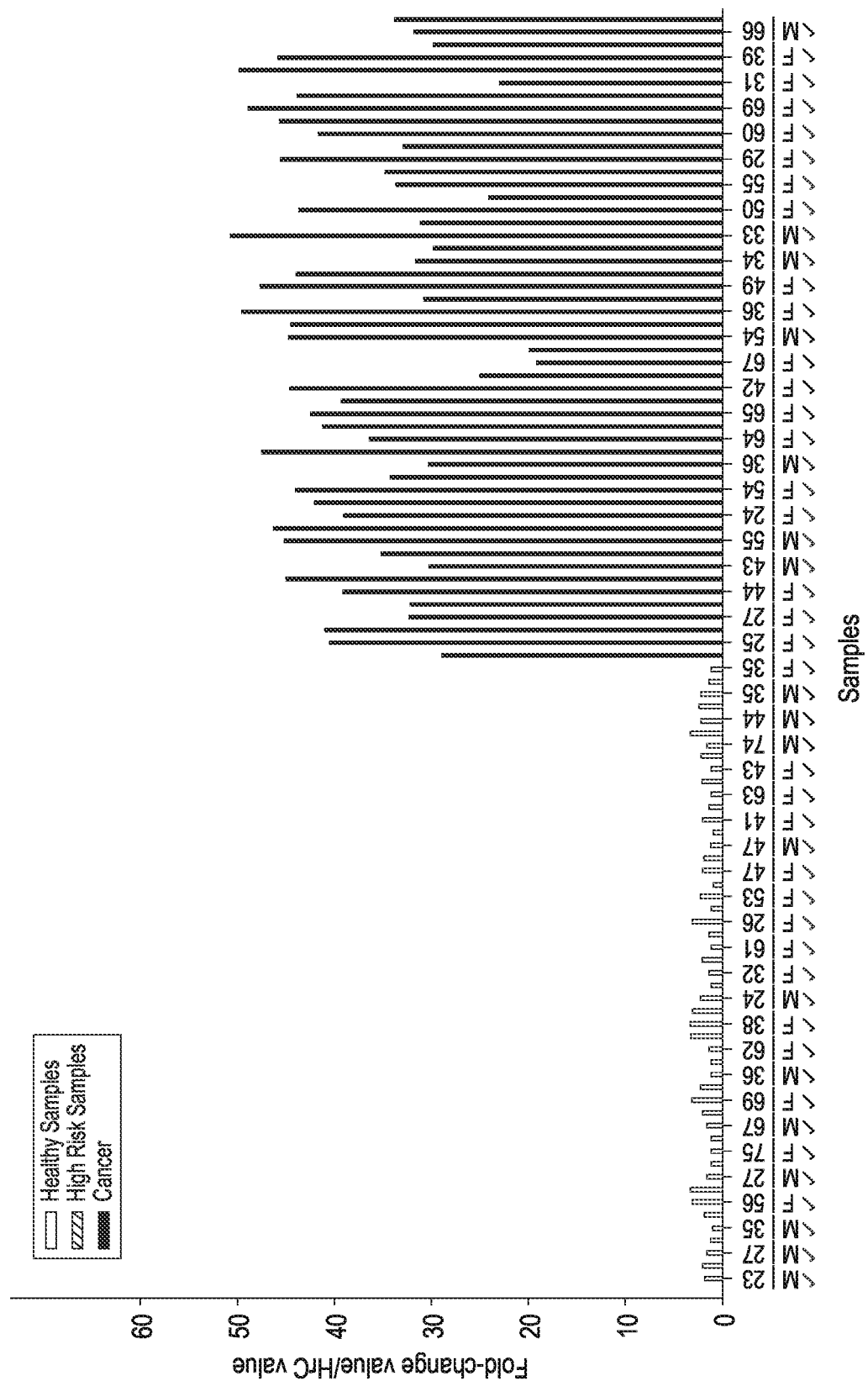

FIG. 14 depicts a representative sixth graph showing the fold-change value for at least one biomarker of pluripotent stem cell as disclosed in the present study with a cohort of 1000 samples study, in accordance with an embodiment of the present disclosure. The tick marks below show concurrence with the actual clinical status by an independent reviewer in the blinded study.

Figure 15:
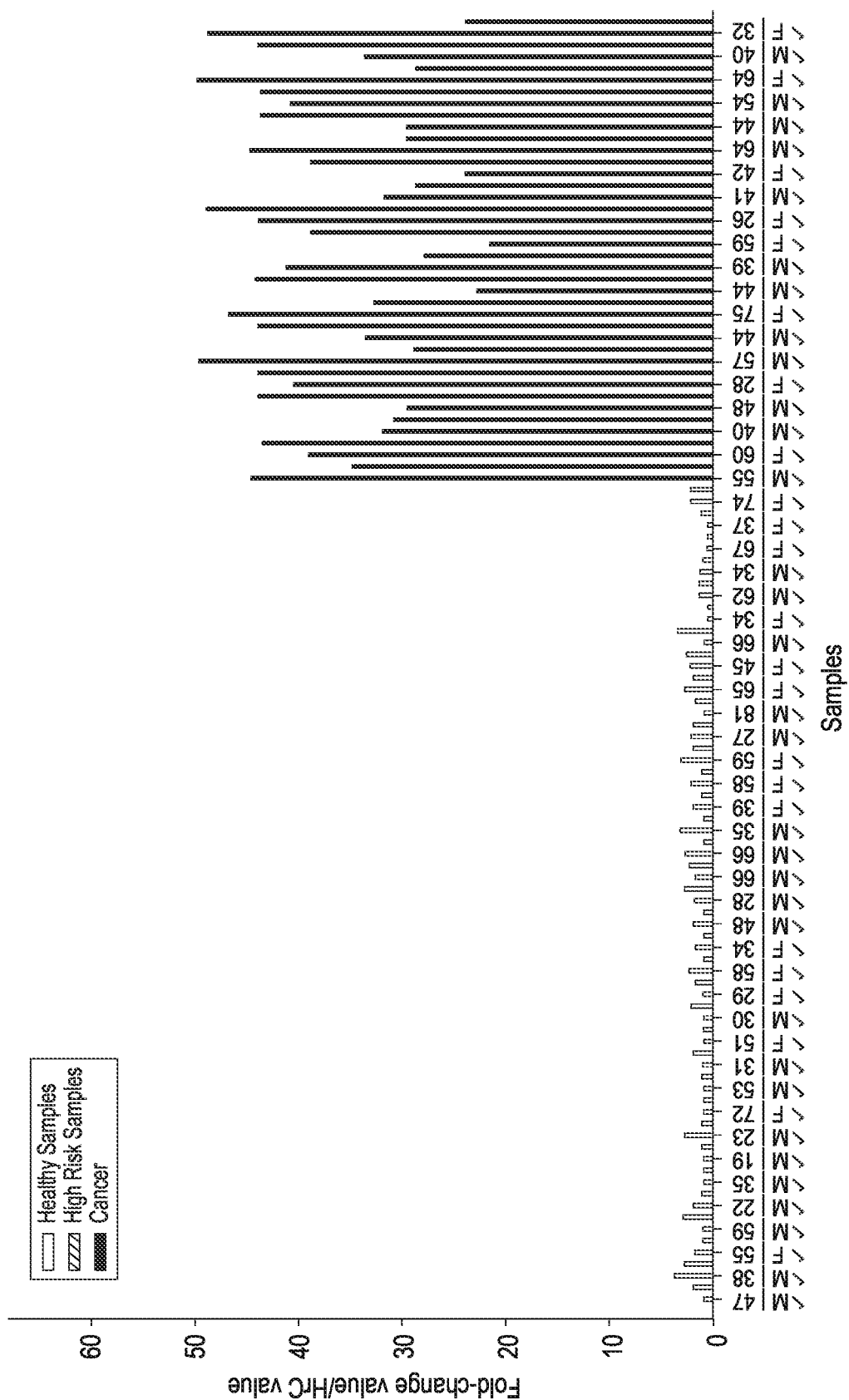

FIG. 15 depicts a representative seventh graph showing the fold-change value for at least one biomarker of pluripotent stem cell as disclosed in the present study with a cohort of 1000 samples study, in accordance with an embodiment of the present disclosure. The tick marks below show concurrence with the actual clinical status by an independent reviewer in the blinded study.

Figure 16:
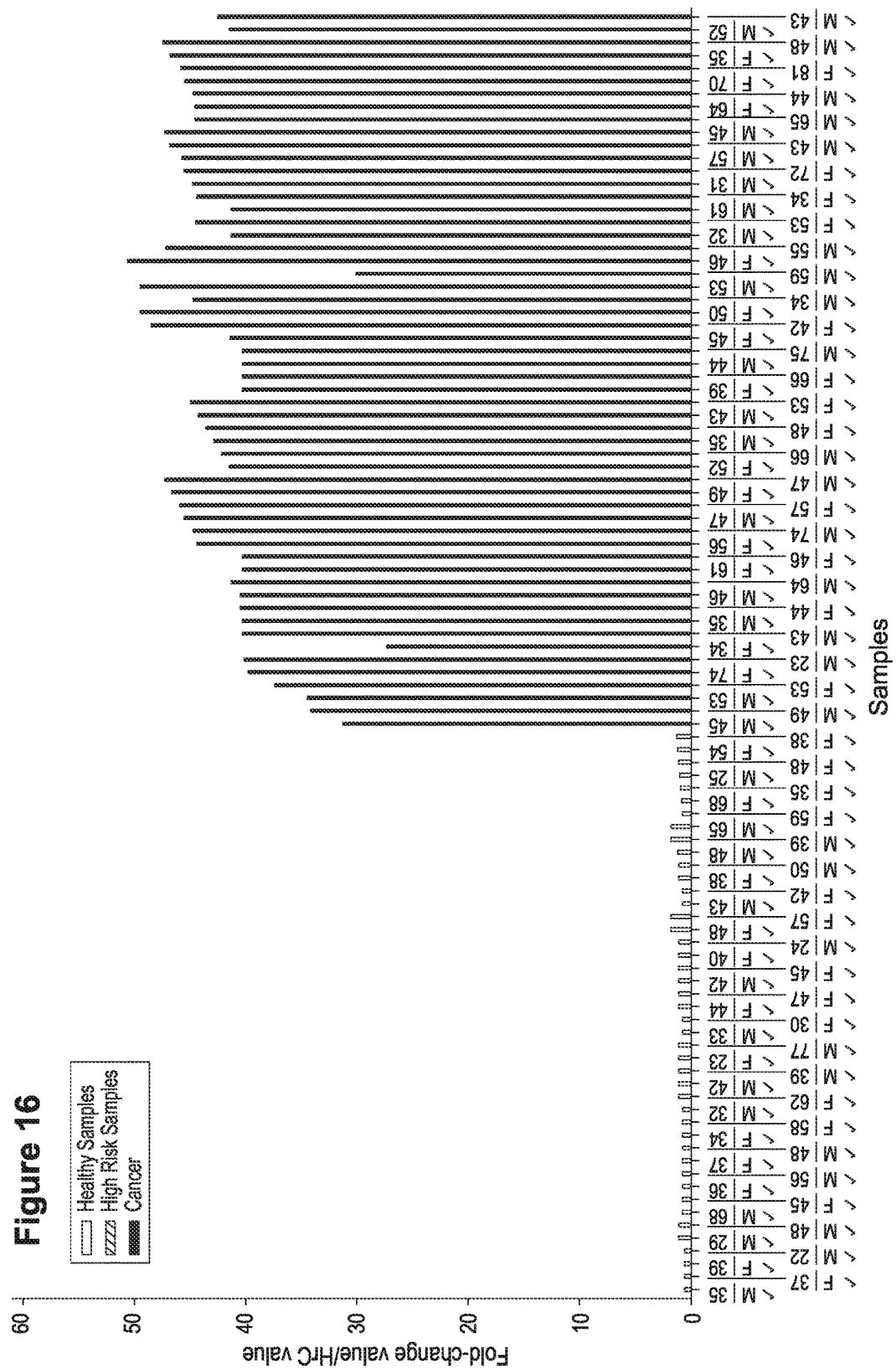

FIG. 16 depicts a representative eighth graph showing the fold-change value for at least one biomarker of pluripotent stem cell as disclosed in the present study with a cohort of 1000 samples study, in accordance with an embodiment of the present disclosure. The tick marks below show concurrence with the actual clinical status by an independent reviewer in the blinded study.

Figure 17:
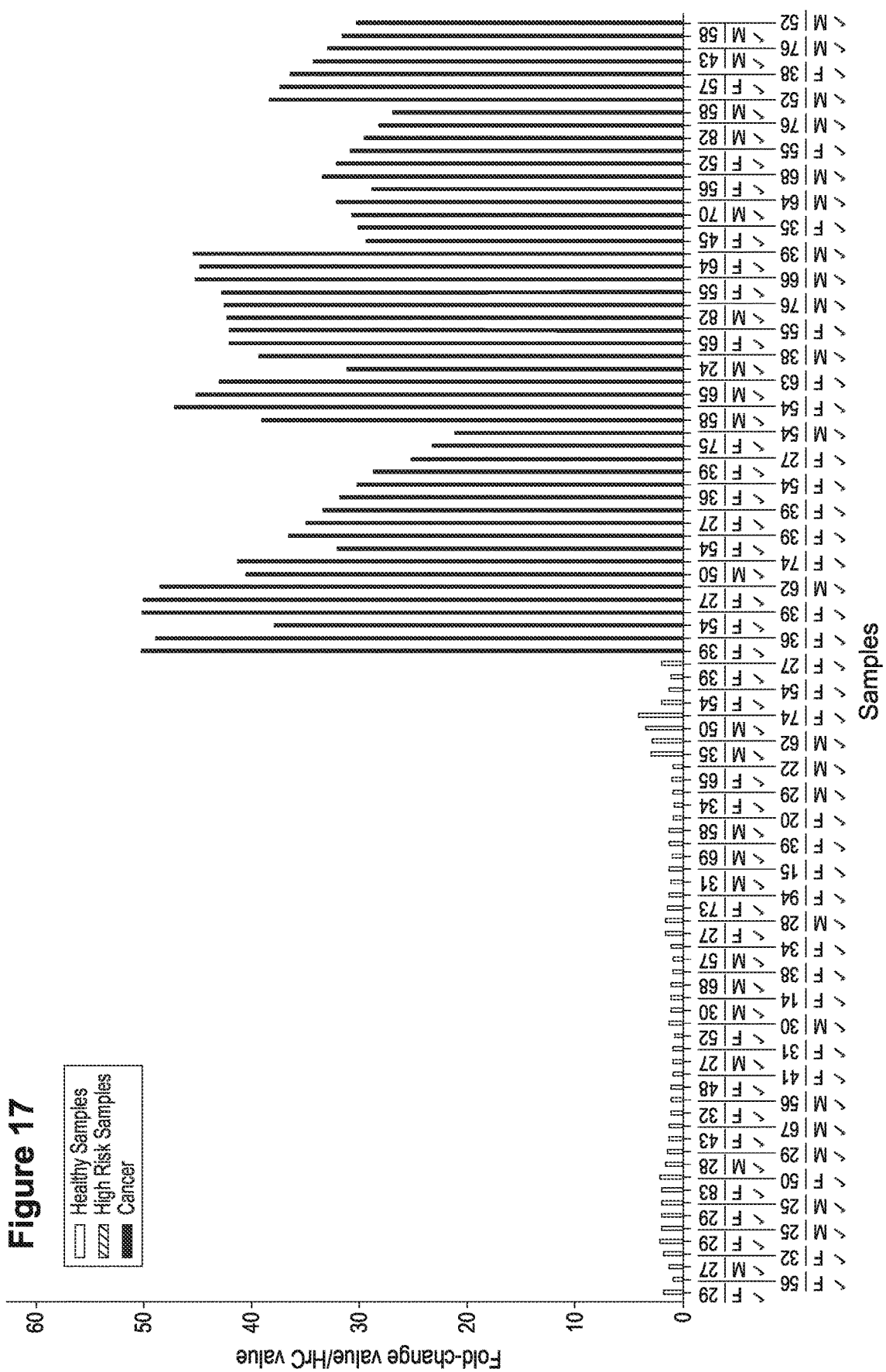

FIG. 17 depicts a representative ninth graph showing the fold-change value of for least one biomarker of pluripotent stem cell as disclosed in the present study with a cohort of 1000 samples study, in accordance with an embodiment of the present disclosure. The tick marks below show concurrence with the actual clinical status by an independent reviewer in the blinded study.

FIG. 18 depicts a representative tenth graph showing the fold-change value for at least one biomarker of pluripotent stem cell as disclosed in the present study with a cohort of 1000 samples study, in accordance with an embodiment of the present disclosure. The tick marks below show concurrence with the actual clinical status by an independent reviewer in the blinded study.

DETAILED DESCRIPTION OF THE INVENTION

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

Definitions

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited For example, a ratio of about 1:1 to 1:20 should be interpreted to include not only the explicitly recited limits of about 1:1 to about 1:20, but also to include sub-ranges, such as 1:2 to 1:10, 1:2 to 1:15, and so forth, as well as individual amounts, including fractional amounts, within the specified ranges, such as 1:2.5, and 1:16.3, for example.

The term "cancer" refers to the physiological condition in animals that is characterized by unregulated cell growth. The term "cancer" as used in the present disclosure is intended to include benign and malignant cancers, dormant tumours or micro-metastases. The types of cancer include, but are not limited to, carcinoma, lymphoma, blastoma (including medulloblastoma and retinoblastoma), sarcoma (including liposarcoma and synovial cell sarcoma), neuroendocrine tumours (including carcinoid tumours, gastrinoma, and islet cell cancer), mesothelioma, schwannoma (including acoustic neuroma), meningioma, adenocarcinoma, melanoma, and leukaemia or lymphoid malignancies. More particular examples of cancers include breast cancer, liver cancer, ovarian cancer, lung cancer, leukaemia, prostate cancer, lymphoma, pancreatic cancer, cervical cancer, colon cancer, osteosarcoma, testicular cancer, thyroid cancer, gastric cancer, Ewing sarcoma, bladder cancer, gastrointestinal stromal tumour (GIST), kidney cancer (e.g., renal cell carcinoma), squamous cell cancer (e.g., epithelial squamous cell cancer), lung cancer (including small-cell lung cancer (SCLC), non-small cell lung cancer (NSCLC), adenocarcinoma of the lung, squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, hepatoma, breast cancer (including metastatic breast cancer), bladder cancer, colon cancer, rectal cancer, colorectal cancer, endometrial or uterine carcinoma, salivary gland carcinoma, prostate cancer, vulval cancer, thyroid cancer, hepatic carcinoma, anal carcinoma, penile carcinoma, Merkel cell cancer, mycoses fungoids, testicular cancer, oesophageal cancer, tumours of the biliary tract, head and neck cancer, as well as B-cell lymphoma (including low grade/follicular non-Hodgkin's lymphoma (NHL); small lymphocytic (SL) NHL; intermediate grade/follicular NHL; inter mediate grade diffuse NHL; high grade immunoblastic NHL; high grade lymphoblastic NHL; high grade small non-cleaved cell NHL; bulky disease NHL, mantle cell lymphoma; AIDS-related lymphoma; and Waldenstrom's Macroglobulinemia; chronic lymphocytic leukaemia (CLL); acute lymphoblastic leukaemia (ALL); Hairy cell leukaemia; chronic myeloblastic leukaemia; and post-transplant lymphoproliferative disorder (PTLD), as well as abnormal vascular proliferation associated with phakomatoses, edema (such as that associated with brain tumours), and Meigs' syndrome.

The term "advanced stage of cancer" or "cancer at advanced stage" refers to a cancer which has spread outside the site of the organ of origin, either by local origin or by metastasis. The terms "stage-I", "stage-II", "stage-III", and "stage-IV" are well-known terms used to refer to a grade of cancer which has inflicted a patient. The term "pre-cancerous" is used to refer to a stage of cancer where no symptoms of the cancer is visible. The pre-cancerous stage could not be detected by a PET scan. The term "early detection" as it relates to cancer, has been used to describe detection of stage-I, or stage-II cancer. The term "early onset" refers to a cancer at a stage where it is not yet detectable by any one of the conventional methods known in the art. The term "detects" or "detection" refers to a detection which has been performed outside of a patient/subject using a sample from the patient/subject.

The term "predicts", or "prediction" refers to a likelihood of something that will happen in future or in due course of time.

The term "blood sample" refers to the whole blood sample that is obtained from a subject. The scope of the method as disclosed herein begins from the stage of having obtained the blood sample irrespective of the source for the procurement, and the method does not involve any invasive techniques or operating on a subject. The term "blood sample" encompasses any form of processed blood sample also. By "processing", the present disclosure intends to cover any method for enriching a specific population of cells or a mere processing so as to enable the blood sample to be used for testing by "in-vitro" methods.

The term "in-vitro" refers to a task or method or experiment being performed or taking place in a test tube, culture dish, or elsewhere outside a living organism.

The term "reference" refers to at least one selected from a group consisting of: (a) blood sample obtained prior to administering anti-cancer therapy; (b) blood sample obtained prior to the time point at which a blood sample under study is obtained; (c) blood sample obtained at a time point subsequent to which the blood sample under study is obtained; and (d) blood sample obtained from a control. The term "reference level" refers to the expression of at least one biomarker of pluripotent stem cell obtained from the reference. The term "control sample" refers to a blood sample obtained from a non-cancer subject, and the term "expression of at least one biomarker of pluripotent stem cell in a control sample" refers to the expression of the at least one biomarker of pluripotent stem cell as disclosed herein, and the expression is studied using similar steps as is disclosed herein for studying the expression of the biomarker in the blood sample. It is understood that the steps for processing and analysing expression of the biomarker in a control sample is similar to the steps for performing and analysing expression of the biomarker in a blood sample, and the expression levels of the biomarker obtained from the blood sample in compared with the expression levels obtained from the control sample.

The term "expression level" refers to a particular level of expression of a nucleic acid. The nucleic acid can be a DNA or RNA. The DNA is intended to include cDNA, and RNA is intended to include all types of RNA, including mRNA. The term "increase in the expression level" refers to an increased expression or increased levels of a biomarker in an individual relative to a control, such as an individual or individuals who are not suffering from the disease or disorder (e.g., cancer), an internal control (e.g., a housekeeping biomarker), or the level of a biomarker in a sample obtained prior to administration of a therapy.

The term "metabolically altered cell" refers to any cell which is altered metabolically to a form that is not supposed to be present in an environment under normal circumstances. The alteration can be in form of an increase in proliferation.

The term "quiescent cell" refers to a quiescent cell that does not proliferate as per the regulated cell cycle of division.

The term "pluripotent stem cell" refers to cell which has the ability of self-replicating and to give rise to all types of cells in a subject.

The term "biomarker" as used herein refers to a biomolecule which is a nucleic acid and is used to characterize a particular cell population. The term is intended to cover both DNA and RNA forms of nucleic acid. The term "biomarker of pluripotent stem cell" refers to any biomarker which can be used to characterize a population of pluripotent stem cells.

The term "subject" refers to any mammal whose blood sample has been taken for analysis using the in-vitro method of the present disclosure. The exemplification is based on human beings used as subjects.

The term "cancer-free" refers to a subject who has not been diagnosed with cancer. The term "positive response" as used herein refers to a positive response of a subject to anti-cancer therapy which means the therapy is effective in reducing the population of cancerous cells. The term "negative response" as used herein refers that the anti-cancer therapy is not able to reduce the population of cancerous cells or not able to cure the subject of cancer.

The term "invasive" refers to any technique that involves entry into the living body as by way of incision or by way of insertion of an instrument.

The term "at least one biomarker of pluripotent stem cell" refers to a gene which is selected from a group consisting of: Oct-4 (octamer-binding transcription factor 4), Sox-2 (sex determining region Y-box 2), Nanog, p53, NFκB, Sirt-1 (Sirtuin 1), Sirt-6 (Sirtuin 6), NAD (Nicotinamide adenine dinucleotide), RAS, ERC, erbB-2 (Erb-B2 Receptor Tyrosine Kinase 2), ABL (Abelson murine leukemia), subsets thereof, and combinations thereof. The subsets of Oct-4, Sox-2, Nanog, p53, NFκB, Sirt-1, Sirt-6, NAD, RAS, ERC, erbB-2, ABL and combinations thereof are also part of the present disclosure.

The term "cancer-related marker" comprises all the well-known cancer-related marker in the field of cancer study. A non-limiting list of cancer-related markers is mentioned herewith and includes, ABL1, EVI1, MYC, APC, IL2, TNFAIP3, ABL2, EWSR1, MYCL1, ARHGEF12, JAK2, TP53, AKT1, FEV, MYCN, ATM, MAP2K4, TSC1, AKT2, FGFR1, NCOA4, BCL11B, MDM4, TSC2, ATF1, FGFR1OP, NFKB2, BLM, MEN1, VHL, BCL11A, FGFR2, NRAS, BMPR1A, MLH1, WRN, BCL2, FUS, NTRK1, BRCA1, MSH2, WT1, BCL3, GOLGA5, NUP214, BRCA2, NF1, BCL6, GOPC, PAX8, CARS, NF2, BCR, HMGA1, PDGFB, CBFA2T3, NOTCH1, BRAF, HMGA2, PIK3CA, CDH1, NPM1, CARD11, HRAS, PIM1, CDH11, NR4A3, CBLB, IRF4, PLAG1, CDK6, NUP98, CBLC, JUN, PPARG, CDKN2C, PALB2, CCND1, KIT, PTPN11, CEBPA, PML, CCND2, KRAS, RAF1, CHEK2, PTEN, CCND3, LCK, REL, CREB1, RB1, CDX2, LMO2, RET, CREBBP, RUNX1, CTNNB1, MAF, ROS1, CYLD, SDHB, DDB2, MAFB, SMO, DDX5, SDHD, DDIT3, MAML2, SS18, EXT1, SMARCA4, DDX6, MDM2, TCL1A, EXT2, SMARCB1, DEK, MET, TET2, FBXW7, SOCS1, EGFR, MITF, TFG, FH, STK11, ELK4, MLL, TLX1, FLT3, SUFU, ERBB2, MPL, TPR, FOXP1, SUZ12, ETV4, MYB, USP6, GPC3, SYK, ETV6, IDH1, TCF3, and combinations thereof. The list provided herein refers to the list of cancer-related markers which are well-known and common to a skilled person in the art. The abbreviated forms are construed to be known to skilled person in the art.

The term "administering" refers to a method of giving a dosage of a compound (e.g., a VEGF antagonist and/or a PD-L1 axis binding antagonist) or a composition (a pharmaceutical composition including a VEGF antagonist and/or a PD-L1 axis binding antagonist) to a patient. The administration can be intramuscular, intravenous, intradermal, percutaneous, intraarterial, intraperitoneal, intralesional, intracranial, intraarticular, intraprostatical, intrapleural, intratracheal, intrathecal, intranasal, intravaginal, intrarectal, topical, intratumoral, peritoneal, subcutaneous, subconjunctival, intravesicular, mucosal, intrapericardial, intraumbilical, intraocular, intraorbital, intravitreal, oral.

The term "anti-cancer therapy" refers to any therapy known in the art for curing/treating cancer.

The term "chemotherapeutic agent" refers to chemical compounds useful in the treatment of cancer.

The term "enriching" as per the present disclosure refers to a process for isolating a required population of cell in a manner that the required population is present at a higher population in the isolated mixture which would be beneficial to analyse a biomarker in such population. The present disclosure mentions "enriching" in a context where it implies to mention a process for increasing concentration of a particular type of pluripotent stem cells so as to enable studies to be carried out for analysing expression level of at least one biomarker of pluripotent stem cell and/or for analysing mutation in nucleic acid obtained from such population of pluripotent stem cell.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The methods currently available for detection of cancer have several drawbacks associated with them. The limitations associated with Positron emission tomography (PET) and circulating tumour cells (CTC) have been described below.

Limitations of PET Scan

Positron emission tomography (PET), now almost 45 years after its initial development, has become an established nuclear imaging modality that has proved especially useful in cancer diagnosis. PET makes use of a tracer molecular known as 18F-2-fluoro-2-deoxy-D-glucose (FDG) (an analogue of glucose). The use of FDG to image glucose metabolic rate takes advantage of the observation, that malignant cells have higher rates of aerobic glycolysis than normal tissues (Griffeth 2005, BUMC Proceedings, 18:321-330). Thus, the malignant cell utilizes more glucose to meet their energy needs. FDG is currently the only agent approved by the Food and Drug Administration (FDA) for oncology studies. Fortunately, while FDG is not a perfect imaging agent (some tumours show poor FDG avidity and some benign processes show high FDG avidity), FDG does work very well in most malignant tumours of clinical importance, with the largest exception being prostate cancer.

Several factors can make the interpretation of PET studies challenging. Chief among these factors in daily practice are variable physiologic uptake of FDG by normal tissues, FDG uptake related to inflammation or infection, occasional malignant lesions with low avidity for FDG, unusual tumour sites, limited resolution of small lesions, altered biodistribution of FDG related to hyperglycemia or hyperinsulinemia, bone marrow activation commonly encountered in cancer patients, and motion artefacts. Unfortunately, glucose uptake is prevalent in cells of the body other than malignant cells. Physiologic uptake in some normal tissues can be highly variable. Although many accumulate FDG to a predictable extent, there are others whose uptake cannot be predicted. For example, the brain typically shows intense uptake of FDG, because it metabolizes glucose exclusively, while myocardial uptake is intense in patients who have not fasted but highly variable in patients who have fasted. Adipose tissue typically shows minimal FDG uptake, but certain adipose deposits (so-called "brown fat") that play a role in thermogenesis can be dramatically activated in a cold or nervous patient. Sometimes, even relatively predictable activity can be confusing. For example, unlike glucose, FDG is not well reabsorbed by the proximal tubules of the kidney. Thus, it can be predicted that intense activity will be seen in the kidneys and bladder. However, focal pooling of excreted activity in a ureter could be confused with a hypermetabolic iliac lymph node metastasis. Inflammatory cells, especially macrophages, can sometimes accumulate FDG to a considerable extent, so inflammatory or infectious sites are sometimes visualized on PET. Granulomatous conditions, such as sarcoidosis, fungal infections, tuberculosis, and *Mycobacterium avium*-intracellular infection, can cause particular problems in the PET evaluation of pulmonary lesions or lymph nodes. Even inflammation related to therapeutic procedures, such as surgery or radiotherapy, can cause significant uptake. When clinically possible, it is usually wise to wait at least 3 months after the completion of radiotherapy before performing a PET study to avoid confusion by inflammatory uptake of FDG. Therefore, it is not possible to perform PET within short span of intervals for checking the response of a patient undergoing cancer treatment, one has to wait for a minimum time period of 3 months to check whether the patient is responding to the treatment. If the patient is not responding, then losing the precious time shall prove to be fatal to the patient.

Some malignant lesions have low avidity for FDG such as prostate, bronchoalveolar cell carcinoma, low-grade sarcomas, certain low-grade non-Hodgkin's lymphomas, and even a few well-differentiated adenocarcinomas of the lung—that may show poor concentration of FDG. Most neuroendocrine tumours are poorly seen on FDG-PET. Small lesions or unusual presentations/locations always make the job of tumour detection and staging more difficult. PET alone is sometimes unable to localize small tumours or confirm whether FDG uptake in unusual sites reflects tumour or nontumor.

Limitations of Circulating Tumour Cells

Despite the numerous scientific publications related to CTC detection in cancer patients, the physician does not use this biomarker in routine clinical practice. This can be explained by the large number of methods available for CTC detection and by the difficulty of the physician and the biologist to select the optimal method (Huang T et al, Biosens Bioelectron 2014; 51:213-8). In this context, it is noteworthy that the only FDA approved method for CTC detection, the CellSearch method (Janssen Diagnostics Company, USA), has been approved for CTC detection in metastatic breast, prostate and colon cancer patients. Contrarily, CTC have been reported to result in false positives and false negative in the detection for breast, prostate and colon cancer (Lori M. Millner et al, Ann Clin Lab Sci. 2013 43(3), because CTCs that have undergone epithelial-mesenchymal transition cannot express epithelial biomarkers, the CellSearch system can certainly miss the detection of a subpopulation of CTCs of interest in several cancer patients (Hofman V J et al, Am J Clin Pathol 2011; 135). Direct technologies for CTC detection in cancer are certainly strongly attractive, but the results obtained by different teams probably need to be validated in independent and large multi-centre studies. Many other methods are currently being developed for CTC characterization, such as a method allowing functional evaluation the CTCs and characterization of a subpopulation of malignant cells (Yao X et al, Integr Biol (Camb) 2014; 6:388-98). Currently these new methods seem to be difficult for translation into the clinical routine practice. These approaches lack a multi-centre assessment program, and thus it is difficult to evaluate their reproducibility, their sensitivity and their specificity.

The existing technique for detecting cancer is based on the specific cancer biomarker isolated from the affected tissue, the method therefore involves invasive methods to isolate the affected tissue for detecting the presence of cancer. The techniques available at present offers detection of cancer which involves invasive technique and for obvious reasons the technique cannot be done frequently on a patient to check for the presence of cancer. Therefore, the existing techniques have drawbacks in terms of difficulty in practising, not able to accurately predict the possibility of cancer with a single practice on the patient, not fit for follow-up cure of the patient. The existing technique can only be used to detect certain type of cancers once they have reached an advanced stage, and the patient having reached an advance stage of the disease has very less chance of surviving the treatment, this is one of the greatest drawbacks of the existing technique.

There exist lacunae in terms of the availability of a simple test which can be performed to detect all types of cancer at an early stage, and which can be performed in a frequent manner to monitor the stage of cancer. The present disclosure discloses a process for detecting and predicting cancer by analysing blood sample of the subject concerned. The present disclosure discloses a process for detecting the grade of cancer that a subject is suffering from, with a simple blood sample. The present disclosure accurately detects the type of cancer with a simple blood sample, thereby without using any invasive techniques such as biopsy. The process of the present disclosure predicts the possibility of a subject getting inflicted with cancer with only a blood sample. The present disclosure detects pre-cancerous stage even before any symptoms start to appear, thus providing a significant advantage over conventional methods of detection which can only detect cancer once it has reached a certain level in the body. The present disclosure also discloses a process for enriching pluripotent stem cells (PSC) which can further be used for evaluating stem cell markers on PSC. Thus, the present disclosure discloses a simple, efficient, and highly accurate process for detecting and predicting cancer by analysing a simple blood sample from a subject.

The present disclosure discloses in-vitro methods for detecting presence of cancer, predicting the chances of getting inflicted with cancer, grading stage of cancer, monitoring cancer progression, monitoring response to anti-cancer treatment, follow-up check to confirm whether cancer has been eradicated from the subject concerned. The in-vitro method as disclosed herein also provides accurate information about specific type of cancer with only a blood sample and not involving any invasive techniques. The method as disclosed herein provides the information regarding type of cancer much before the manifestation of conditions which are detectable by known techniques such as PET scan, thereby, detecting the presence of specific type of cancer without having the need to perform biopsy. Also, to enable a doctor to target a specific tissue of organ for performing biopsy, the patient needs to show particular symptoms, but in case of cancer the symptoms may appear at an advanced stage thereby reducing the chances of patient's survival, the in-vitro method of present disclosure not only detects the presence of cancer but also detects the primary site of cancer and its type much before the manifestation of symptoms with only a blood sample. The method as disclosed in the present disclosure poses all the above-mentioned uses working only with a blood sample.

The simplicity of the method poses the benefit of being able to use this method frequently while treating a patient for cancer, as against the use of PET scan which can be done with a minimum interval of 6 months. The methods as disclosed herein are in-vitro methods and free of any invasive techniques. The method as disclosed in the present disclosure can detect/predict any cancer in a subject by analysing the blood sample of the subject, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell with a control, wherein an increase in the expression level of the at least one biomarker as compared to the control detects/predicts cancer. The method as disclosed in the present disclosure is capable of detecting presence of metabolically altered cells/quiescent cells by analysing a blood sample by a method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell with a control, wherein an increase in the expression level of the at least one biomarker as compared to the control detects the presence of metabolically altered cells. The method as disclosed in the present disclosure is capable of monitoring response to cancer treatment by analysing a blood sample, said method comprises: (a) obtaining a blood sample at one time point following an anti-cancer therapy; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference that monitors the response to cancer treatment.

The present disclosure discloses a method for detecting presence of cancer and also for detecting a specific type of cancer from a blood sample, said method comprises: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell with a control, wherein an increase in the expression level of the at least one biomarker as compared to the control indicates presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed.

The method as disclosed in the present disclosure is used for detecting and predicting pre-cancerous stage, stage-I cancer, stage-II cancer, stage-III cancer, and stage IV cancer, wherein the cancer is selected from a non-limiting group consisting of ovarian cancer, breast cancer, prostate cancer, lung cancer, liver cancer, colon cancer, leukaemia, lymphoma, bladder cancer, renal cancer, thyroid cancer, pancreatic cancer. It is contemplated that other varieties of cancer types can also be included in the present disclosure.

The present disclosure is not to be limited in scope by the specific embodiments described herein, which are intended for the purposes of exemplification only. Functionally-equivalent products, compositions, and methods are clearly within the scope of the disclosure, as described herein.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

In an embodiment of the present disclosure, there is provided an in-vitro method for detecting presence of metabolically altered cells, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects the presence of metabolically altered cells.

In an embodiment of the present disclosure, there is provided an in-vitro method for detecting presence of metabolically altered cells, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects the presence of metabolically altered cells, and wherein the method further comprises analysing the nucleic acid by performing sequence-based assays.

In an embodiment of the present disclosure, there is provided an in-vitro method for detecting presence of metabolically altered cells as described herein, wherein the increase in the expression level of the at least one biomarker of pluripotent stem cell is at least 2 folds as compared to the control. In another embodiment, the increase in the expression level of the at least one biomarker of pluripotent stem cell is at least 3 folds as compared to the control. In yet another embodiment, the increase in the expression level of the at least one biomarker of pluripotent stem cell is at least 5 folds as compared to the control.

In an embodiment of the present disclosure, there is provided an in-vitro method for detecting presence of metabolically altered cells as described herein, wherein the increase in the expression level of the at least one biomarker of pluripotent stem cell is in a range of 10-20 folds as compared to the control. In another embodiment, the increase in the expression level of the at least one biomarker of pluripotent stem cell is in a range of 20-30 folds as compared to the control. In yet another embodiment, the increase in the expression level of the at least one biomarker of pluripotent stem cell is in a range of 30-40 folds as compared to the control. In one another embodiment, the increase in the expression level of the at least one biomarker of pluripotent stem cell is in a range of 40-50 folds as compared to the control.

In an embodiment of the present disclosure, there is provided an in-vitro method for detecting presence of metabolically altered cells as described herein, wherein the at least one biomarker of pluripotent stem cell is selected from a group consisting of Oct-4, Sox-2, Nanog, p53, Sirt-1, Sirt-6, Sirt-3, NAD, RAS, ERC, erbB-2, ABL, subsets thereof, and combinations thereof. In another embodiment, the at least one biomarker of pluripotent stem cell is Oct-4. In yet another embodiment, the at least one biomarker of pluripotent stem cell is Oct-4a. In an alternate embodiment, the at least one biomarker of pluripotent stem cell is Oct-4b.

In an embodiment of the present disclosure, there is provided an in-vitro method for detecting presence of metabolically altered cells as described herein, wherein the at least one biomarker of pluripotent stem cell is selected from a group consisting of Oct-4, Sox-2, Nanog, p53, Sirt-1, Sirt-6, Sirt-3, subsets thereof, and combinations thereof. In another embodiment, the at least one biomarker of pluripotent stem cell is Sox-2. In yet another embodiment, the at least one biomarker of pluripotent stem cell is Nanog. In an alternate embodiment, the at least one biomarker of pluripotent stem cell is p53. In one another embodiment, the at least one biomarker of pluripotent stem cell is Sirt-1. In another alternate embodiment, the at least one biomarker of pluripotent stem cell is Sirt-6. In yet another alternate embodiment, the at least one biomarker of pluripotent stem cell is Sirt-3.

In an embodiment of the present disclosure, there is provided an in-vitro method for detecting presence of metabolically altered cells as described herein, wherein obtaining the nucleic acid from the mixture is by any one method selected from a group consisting of: (a) guanidinium thiocyanate-phenol-chloroform nucleic acid extraction; (b) cesium chloride gradient centrifugation method; (c) cetyltrimethylammonium bromide nucleic acid extraction; (d) alkaline extraction; (e) resin-based extraction; and (f) solid phase nucleic acid extraction.

In an embodiment of the present disclosure, there is provided an in-vitro method for detecting presence of metabolically altered cells as described herein, wherein performing an assay with the nucleic acid for analysing the expression of the at least one biomarker is done by a technique selected from a group consisting of: quantitative PCR, flow cytometry, and Next Generation Sequencing (NGS).

In an embodiment of the present disclosure, there is provided an in-vitro method for detecting presence of metabolically altered cells as described herein, wherein the control is the expression level of the at least one biomarker of pluripotent stem cells obtained from a cancer-free subject.

In an embodiment of the present disclosure, there is provided an in-vitro method for detecting presence of metabolically altered cells as described herein, wherein the enriching of the pluripotent stem cells from the blood sample comprises: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain enriched pluripotent stem cells.

In an embodiment of the present disclosure, there is provided an in-vitro method for detecting presence of metabolically altered cells as described herein, wherein the enriching of the pluripotent stem cells from the blood sample comprises: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain enriched pluripotent stem cells, and wherein the processing of the second mixture comprises, at least one method selected from a group consisting of: (a) extraction process; (b) washing process; (c) centrifugation process, and combinations thereof.

In an embodiment of the present disclosure, there is provided an in-vitro method for detecting presence of metabolically altered cells as described herein, wherein the method is independent of invasive techniques.

In an embodiment of the present disclosure, there is provided an in-vitro method for detecting presence of metabolically altered cells as described herein, wherein the nucleic acid is DNA. In another embodiment, the nucleic acid is RNA.

In an embodiment of the present disclosure, there is provided an in-vitro method for detecting presence of quiescent cells, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects the presence of quiescent cells.

In an embodiment of the present disclosure, there is provided an in-vitro method for detecting presence of quiescent cells, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects the presence of quiescent cells, and wherein the method further comprises analysing the nucleic acid by performing sequence-based assays.

In an embodiment of the present disclosure, there is provided an in-vitro method for detecting presence of quiescent cells, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects the presence of quiescent cells, and wherein the increase is at most 1.9 folds. In another embodiment, the increase is in a range of 0.1-1.9 folds. In yet another embodiment, the increase is in a range of 0.2-1.8 folds.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level is in a range of 10-20 folds as compared to the control and detects stage-I cancer.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level is in a range of 20-30 folds as compared to the control and detects stage-II cancer.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level is in a range of 30-40 folds as compared to the control and detects stage-III cancer.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level is 40 folds or higher as compared to the control and detects stage-IV cancer.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level is in a range of 6-10 folds as compared to the control and detects pre-cancerous stage.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the method further comprises analysing the nucleic acid by performing sequence-based assays. In another embodiment of the present disclosure, analysing the nucleic acid by sequence-based assays detects the type of cancer.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d)

performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level of the at least one biomarker of pluripotent stem cell is at least 2 folds as compared to the control. In another embodiment, the increase in the expression level of the at least one biomarker of pluripotent stem cell is at least 3 folds as compared to the control. In yet another embodiment, the increase in the expression level of the at least one biomarker of pluripotent stem cell is at least 5 folds as compared to the control.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level of the at least one biomarker of pluripotent stem cell is at least 6 folds, or 7 folds, or 8 folds, or 9 folds, or 10 folds as compared to the control.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the increase in the expression level of the at least one biomarker of pluripotent stem cell is in a range of 10-20 folds as compared to the control. In another embodiment, the increase in the expression level of the at least one biomarker of pluripotent stem cell is in a range of 20-30 folds as compared to the control. In yet another embodiment, the increase in the expression level of the at least one biomarker of pluripotent stem cell is in a range of 30-40 folds as compared to the control. In one another embodiment, the increase in the expression level of the at least one biomarker of pluripotent stem cell is 40 folds or higher as compared to the control.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the at least one biomarker of pluripotent stem cell is selected from a group consisting of Oct-4, Sox-2, Nanog, p53, Sirt-1, Sirt-6, Sirt-3, NAD, RAS, ERC, erbB-2, ABL, subsets thereof, and combinations thereof. In another embodiment, the at least one biomarker of pluripotent stem cell is Oct-4, and subsets thereof. In yet another embodiment, the at least one biomarker of pluripotent stem cell is Oct-4a. In one another embodiment, the at least one biomarker of pluripotent stem cell is Oct-4b.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the at least one biomarker of pluripotent stem cell is selected from a group consisting of Oct-4, Sox-2, Nanog, p53, Sirt-1, Sirt-6, Sirt-3, subsets thereof, and combinations thereof. In another embodiment, the at least one biomarker of pluripotent stem cell is Sox-2, and subsets thereof. In yet another embodiment, the at least one biomarker of pluripotent stem cell is Nanog, and subsets thereof. In one another embodiment, the at least one biomarker of pluripotent stem cell is p53, and subsets thereof. In alternate embodiment, the at least one biomarker of pluripotent stem cell is Sirt-1, and subsets thereof. In a still alternate embodiment, the at least one biomarker of pluripotent stem cell is Sirt-6, and subsets thereof. In one another alternate embodiment, the at least one biomarker of pluripotent stem cell is Sirt-3, and subsets thereof.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the at least one biomarker of pluripotent stem cell is selected from a group consisting of NAD, RAS, ERC, erbB-2, ABL, subsets thereof, and combinations thereof. In another embodiment, the at least one biomarker of pluripotent stem cell is NAD, and subsets thereof. In yet another embodiment, the at least one biomarker of pluripotent stem cell is RAS, and subsets thereof. In still another embodiment, the at least one biomarker of pluripotent stem cell is ERC, and subsets thereof. In one another embodiment, the at least one biomarker of pluripotent stem cell is erbB-2, and subsets thereof. In an alternate embodiment, the at least one biomarker of pluripotent stem cell is ABL, and subsets thereof.

In an embodiment of the present disclosure, there is provided an in-vitro method for detecting cancer as described herein, wherein obtaining the nucleic acid from the mixture is by any one method selected from a group consisting of: (a) guanidinium thiocyanate-phenol-chloroform nucleic acid extraction; (b) cesium chloride gradient centrifugation method; (c) cetyltrimethylammonium bromide nucleic acid extraction; (d) alkaline extraction; (e) resin-based extraction; and (f) solid phase nucleic acid extraction.

In an embodiment of the present disclosure, there is provided an in-vitro method for detecting cancer as described herein, wherein the nucleic acid is DNA. In another embodiment, the nucleic acid is RNA.

In an embodiment of the present disclosure, there is provided an in-vitro method for detecting cancer as described herein, wherein performing an assay with the nucleic acid for analysing the expression of the at least one biomarker is done by a technique selected from a group consisting of: quantitative PCR, flow cytometry, and Next Generation Sequencing (NGS).

In an embodiment of the present disclosure, there is provided an in-vitro method for detecting cancer as described herein, wherein the control is the expression level of the at least one biomarker of pluripotent stem cells obtained from a cancer-free subject.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects cancer, and wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; and (iii) processing the second mixture to obtain enriched pluripotent stem cells, and wherein processing of the second mixture comprises at least one method selected from a group consisting of: (1) extraction process; (2) washing process; (3) centrifugation process, and combinations thereof. In another embodiment, the centrifugation process can include sequential centrifugation to obtain pluripotent stem cells.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, wherein the at least one biomarker of pluripotent stem cell is selected from a group consisting of Oct-4, Sox-2, Nanog, p53, Sirt-1, Sirt-6, Sirt-3, NAD, RAS, ERC, erbB-2, ABL, subsets thereof, and combinations thereof. In another embodiment, the at least one biomarker of pluripotent stem cell is Oct-4 and subsets thereof. In yet another embodiment, the at least one biomarker of pluripotent stem cell is Oct-4a. In still another embodiment, the at least one biomarker of pluripotent stem cell is Oct-4b.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, wherein the at least one biomarker of pluripotent stem cell is selected from a group consisting of Oct-4, Sox-2, Nanog, p53, Sirt-1, Sirt-6, Sirt-3, subsets thereof, and combinations thereof. In another embodiment, the at least one biomarker of pluripotent stem cell is Sox-2, and subsets thereof. In yet another embodiment, the at least one biomarker of pluripotent stem cell is Nanog, and subsets thereof. In one another embodiment, the at least one biomarker of pluripotent stem cell is p53, and subsets thereof. In alternate embodiment, the at least one biomarker of pluripotent stem cell is Sirt-1, and subsets thereof. In a still alternate embodiment, the at least one biomarker of pluripotent stem cell is Sirt-6, and subsets thereof. In a yet alternate embodiment, the at least one biomarker of pluripotent stem cell is Sirt-3, and subsets thereof.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, wherein the at least one biomarker of pluripotent stem cell is selected from a group consisting of NAD, RAS, ERC, erbB-2, ABL, subsets thereof, and combinations thereof. In another embodiment, the at least one biomarker of pluripotent stem cell is NAD, and subsets thereof. In yet another embodiment, the at least one biomarker of pluripotent stem cell is RAS, and subsets thereof. In still another embodiment, the at least one biomarker of pluripotent stem cell is ERC, and subsets thereof. In one another embodiment, the at least one biomarker of pluripotent stem cell is erbB-2, and subsets thereof. In an alternate embodiment, the at least one biomarker of pluripotent stem cell is ABL, and subsets thereof.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, wherein the sequence-based assay is either a whole genome sequencing, or transcriptome sequencing of the nucleic acid. It is contemplated that any sequencing technique well-known in the art can be used for sequencing. In one of the embodiment sequence-based assay is performed using Next Generation Sequencing.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein obtaining the nucleic acid from the mixture is by any one method selected from a group consisting of: (a) guanidinium thiocyanate-phenol-chloroform nucleic acid extraction; (b) cesium chloride gradient centrifugation method; (c) cetyltrimethylammonium bromide nucleic acid extraction; (d) alkaline extraction; (e) resin-based extraction; and (f) solid phase nucleic acid extraction.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein performing an assay with the nucleic acid for analysing the expression of the at least one biomarker is done by a technique selected from a group consisting of: quantitative PCR, flow cytometry, and Next Generation Sequencing (NGS).

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein the control is the expression level of the at least one biomarker of pluripotent stem cells obtained from a cancer-free subject.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, and wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; and (iii) processing the second mixture to obtain enriched pluripotent stem cells. In another embodiment, the processing of the second mixture comprises, at least one method selected from a group consisting of: (1) extraction process; (2) washing process; (3) centrifugation process, and combinations thereof. In yet another embodiment, the at least one salt solution is sodium chloride, and the at least one neutral buffer is Ficoll hypaque solution.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, and wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; (iii) centrifuging the second mixture at a speed in a range of 1000-6000 rpm, for a time period in a range of 5-20 minutes, to obtain a supernatant and a pellet; (iv) washing and extracting the pellet or supernatant, to obtain a third mixture; and (v) performing sequential centrifugation with the third mixture for 2-8 rounds with varying speed ranging from 1000-10,000 rpm, to obtain enriched pluripotent stem cells, and wherein the at least one salt solution is sodium chloride, and the at least one neutral buffer is Ficoll hypaque solution.

In an embodiment of the present disclosure, there is provided an in-vitro method for detecting cancer as described herein, wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; (iii) centrifuging the second mixture at a speed in a range of 1000-6000 rpm, for a time period in a range of 5-20 minutes, to obtain a supernatant and a pellet; (iv) washing and extracting the pellet or supernatant, to obtain a third mixture; and (v) performing sequential centrifugation with the third mixture for 2-8 rounds with varying speed ranging from 1000-10,000 rpm, to obtain enriched pluripotent stem cells, and wherein the at least one salt solution is sodium chloride, and the at least one neutral buffer is Ficoll hypaque solution.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, and wherein the cancer-related marker is selected from well-known cancer-related markers in the art. In another embodiment, the cancer-related marker is selected from a group consisting of ABL1, EVI1, MYC, APC, IL2, TNFAIP3, ABL2, EWSR1, MYCL1, ARHGEF12, JAK2, TP53, AKT1, FEV, MYCN, ATM, MAP2K4, TSC1, AKT2, FGFR1, NCOA4, BCL11B, MDM4, TSC2, ATF1, FGFR1OP, NFKB2, BLM, MEN1, VHL, BCL11A, FGFR2, NRAS, BMPR1A, MLH1, WRN, BCL2, FUS, NTRK1, BRCA1, MSH2, WT1, BCL3, GOLGA5, NUP214, BRCA2, NF1, BCL6, GOPC, PAX8, CARS, NF2, BCR, HMGA1, PDGFB, CBFA2T3, NOTCH1, BRAF, HMGA2, PIK3CA, CDH1, NPM1, CARD11, HRAS, PIM1, CDH11, NR4A3, CBLB, IRF4, PLAG1, CDK6, NUP98, CBLC, JUN, PPARG, CDKN2C, PALB2, CCND1, KIT, PTPN11, CEBPA, PML, CCND2, KRAS, RAF1, CHEK2, PTEN, CCND3, LCK, REL, CREB1, RB1, CDX2, LMO2, RET, CREBBP, RUNX1, CTNNB1, MAF, ROS1, CYLD, SDHB, DDB2, MAFB, SMO, DDX5, SDHD, DDIT3, MAML2, SS18, EXT1, SMARCA4, DDX6, MDM2, TCL1A, EXT2, SMARCB1, DEK, MET, TET2, FBXW7, SOCS1, EGFR, MITF, TFG, FH, STK11, ELK4, MLL, TLX1, FLT3, SUFU, ERBB2, MPL, TPR, FOXP1, SUZ12, ETV4, MYB, USP6, GPC3, SYK, ETV6, IDH1, TCF3, and combinations thereof. It can be contemplated that the type of cancer detected shall be based on the cancer-related marker that is analysed for mutation and when desirable mutations have been found. It is also understood that as per the present embodiment, the information regarding type of cancer and the stage of cancer can be achieved with only a blood sample without the need for performing biopsy or other invasive procedures.

In an embodiment of the present disclosure, there is provided an in-vitro method for detecting cancer, said method comprising: (a) obtaining a blood sample; (b) enriching pluripotent stem cells from the blood sample, to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample detects presence of cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed, and wherein the increase in the expression level of the at least one biomarker of pluripotent stem cell is at least 2 folds as compared to the control. In another embodiment, the increase in the expression level of the at least one biomarker of pluripotent stem cell is at least 3 folds as compared to the control. In yet another embodiment, the increase in the expression level of the at least one biomarker of pluripotent stem cell is at least 5 folds as compared to the control. In still another embodiment, the increase in the expression level of the at least one biomarker of pluripotent stem cell is in a range of 10-20 folds as compared to the control. In an alternate embodiment, the increase in the expression level of the at least one biomarker of pluripotent stem cell is in a range of 20-30 folds as compared to the control. In another alternate embodiment, the increase in the expression level of the at least one biomarker of pluripotent stem cell is in a range of 30-40 folds as compared to the control. In one another embodiment, the increase in the expression level of the at least one biomarker of pluripotent stem cell is 40 folds or higher as compared to the control.

In an embodiment of the present disclosure, there is provided an in-vitro method for detecting cancer as described herein, wherein the method is independent of invasive techniques.

In an embodiment of the present disclosure, there is provided an in-vitro method for predicting cancer, said method comprising: (a) obtaining a blood sample; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; and (e) comparing the expression level of the at least one biomarker of pluripotent stem cell in the sample with an expression level of the at least one biomarker in a control sample, wherein an increase in the expression level of the at least one biomarker in the sample as compared to the expression level of the at least one biomarker in the control sample predicts cancer.

In an embodiment of the present disclosure, there is provided an in-vitro method for predicting cancer as described herein, wherein the increase in the expression level of the at least one biomarker of pluripotent stem cell is at least 2 folds as compared to the control. In another embodiment, the increase in the expression level of the at least one biomarker of pluripotent stem cell is at least 3 folds as compared to the control. In yet another embodiment, the increase in the expression level of the at least one biomarker of pluripotent stem cell is at least 5 folds as compared to the control. In an alternate embodiment, the increase in the expression level of the at least one biomarker of pluripotent stem cell is 2 folds, or 3 folds, or 4 folds, or 5 folds, or 6 folds, or 7 folds, or 8 folds, or 9 folds, or 10 folds, as compared to the control.

In an embodiment of the present disclosure, there is provided an in-vitro method for predicting cancer as described herein, wherein the increase in the expression level of the at least one biomarker of pluripotent stem cell is in a range of 10-20 folds as compared to the control. In another embodiment, the increase in the expression level of the at least one biomarker of pluripotent stem cell is in a range of 20-30 folds as compared to the control. In yet another embodiment, the increase in the expression level of the at least one biomarker of pluripotent stem cell is in a range of 30-40 folds as compared to the control. In one another embodiment, the increase in the expression level of the at least one biomarker of pluripotent stem cell is in a range of 40-50 folds as compared to the control.

In an embodiment of the present disclosure, there is provided an in-vitro method for predicting cancer as described herein, wherein the at least one biomarker of pluripotent stem cell is selected from a group consisting of Oct-4, Sox-2, Nanog, p53, Sirt-1, Sirt-6, Sirt-3, NAD, RAS, ERC, erbB-2, ABL, subsets thereof, and combinations thereof. In another embodiment, the at least one biomarker of pluripotent stem cell is Oct-4. In yet another embodiment, the at least one biomarker of pluripotent stem cell is Oct-4a. In an alternate embodiment, the at least one biomarker of pluripotent stem cell is Oct-4b.

In an embodiment of the present disclosure, there is provided an in-vitro method for predicting cancer as described herein, wherein the at least one biomarker of pluripotent stem cell is selected from a group consisting of Oct-4, Sox-2, Nanog, p53, Sirt-1, Sirt-6, Sirt-3, subsets thereof, and combinations thereof. In another embodiment, the at least one biomarker of pluripotent stem cell is Sox-2, and subsets thereof. In yet another embodiment, the at least one biomarker of pluripotent stem cell is Nanog, and subsets thereof. In still another embodiment, the at least one biomarker of pluripotent stem cell is p53, and subsets thereof. In an alternate embodiment, the at least one biomarker of pluripotent stem cell is Sirt-1, and subsets thereof. In another alternate embodiment, the at least one biomarker of pluripotent stem cell is Sirt-6, and subsets thereof. In a still another alternate embodiment, the at least one biomarker of pluripotent stem cell is Sirt-3, and subsets thereof.

In an embodiment of the present disclosure, there is provided an in-vitro method for predicting cancer as described herein, wherein the at least one biomarker of pluripotent stem cell is selected from a group consisting of NAD, RAS, ERC, erbB-2, ABL, subsets thereof, and combinations thereof. In another embodiment, the at least one biomarker of pluripotent stem cell is NAD, and subsets thereof. In yet another embodiment, the at least one biomarker of pluripotent stem cell is RAS, and subsets thereof. In still another embodiment, the at least one biomarker of pluripotent stem cell is ERC, and subsets thereof. In an alternate embodiment, the at least one biomarker of pluripotent stem cell is erbB-2, and subsets thereof. In another alternate embodiment, the at least one biomarker of pluripotent stem cell is ABL, and subsets thereof.

In an embodiment of the present disclosure, there is provided an in-vitro method for predicting cancer as described herein, wherein obtaining the nucleic acid from the mixture is by any one method selected from a group consisting of: (a) guanidinium thiocyanate-phenol-chloroform nucleic acid extraction; (b) cesium chloride gradient centrifugation method; (c) cetyltrimethylammonium bromide nucleic acid extraction; (d) alkaline extraction; (e) resin-based extraction; and (f) solid phase nucleic acid extraction.

In an embodiment of the present disclosure, there is provided an in-vitro method for predicting cancer as described herein, wherein performing an assay with the nucleic acid for analysing the expression of the at least one biomarker is done by a technique selected from a group consisting of: quantitative PCR, flow cytometry, and Next Generation Sequencing (NGS).

In an embodiment of the present disclosure, there is provided an in-vitro method for predicting cancer as described herein, wherein the control is the expression level of the at least one biomarker of pluripotent stem cells obtained from a cancer-free subject.

In an embodiment of the present disclosure, there is provided an in-vitro method for predicting cancer as described herein, wherein the enriching of the pluripotent stem cells from the blood sample comprises: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain enriched pluripotent stem cells.

In an embodiment of the present disclosure, there is provided an in-vitro method for predicting cancer as described herein, wherein the enriching of the pluripotent stem cells from the blood sample comprises: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain enriched pluripotent stem cells, and wherein the at least one salt solution is sodium chloride and the neutral buffer is Ficoll-hypaque solution. In another embodiment, the processing of the second mixture comprises, at least one method selected from a group consisting of: (a) extraction process; (b) washing process; (c) centrifugation process, and combinations thereof.

In an embodiment of the present disclosure, there is provided an in-vitro method for predicting cancer as described herein, wherein the method predicts cancer of all types known in the art.

In an embodiment of the present disclosure, there is provided an in-vitro method for predicting cancer as described herein, wherein the method is independent of invasive techniques.

In an embodiment of the present disclosure, there is provided an in-vitro method for predicting cancer as described herein, wherein the method further comprises analysing the nucleic acid by performing sequence-based assays.

In an embodiment of the present disclosure, there is provided an in-vitro method for predicting cancer as described herein, wherein the method further comprises analysing the nucleic acid by performing sequence-based assays, and wherein analysing the nucleic acid by sequence-based assays detects the type of cancer.

In an embodiment of the present disclosure, there is provided an in-vitro method for evaluating effect of a chemotherapeutic agent, said method comprising: (a) obtaining a blood sample at one time point following administering of the chemotherapeutic agent; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference for evaluating effect of the chemotherapeutic agent.

In an embodiment of the present disclosure, there is provided an in-vitro method for evaluating effect of a chemotherapeutic agent as described herein, wherein the reference is at least one selected from a group consisting of: (i) a blood sample obtained prior to administration of chemotherapeutic agent; (ii) a blood sample obtained at a previous time point as compared to the time point mentioned in step (a); (iii) a blood sample obtained at a subsequent time point as compared to the time point mentioned in step (a); and (iv) a blood sample obtained from a cancer-free subject. In another embodiment of the present disclosure, the reference is a blood sample obtained prior to administration of chemotherapeutic agent. In yet another embodiment, the reference is a blood sample obtained at a previous time point as compared to the time point mentioned in step (a). In an alternate embodiment, the reference is a blood sample obtained from a cancer-free subject. In another alternate embodiment, the reference is a blood sample obtained at a subsequent time point as compared to the time point mentioned in step (a).

In an embodiment of the present disclosure, there is provided an in-vitro method for evaluating effect of a chemotherapeutic agent as described herein, wherein a decrease in the expression level of the at least one biomarker of pluripotent stem cell as compared to a reference level indicates a positive response to the cancer treatment, and wherein the reference in selected from a group consisting of (i) a blood sample obtained prior to administration of chemotherapeutic agent; (ii) a blood sample obtained at a previous time point as compared to the time point mentioned in step (a); and (iii) a blood sample obtained from a cancer-free subject. In another embodiment of the present disclosure, the reference is a blood sample obtained prior to administration of chemotherapeutic agent. In yet another embodiment, the reference is a blood sample obtained at a previous time point as compared to the time point mentioned in step (a). In an alternate embodiment, the reference is a blood sample obtained from a cancer-free subject.

In an embodiment of the present disclosure, there is provided an in-vitro method for monitoring response to cancer treatment, said method comprising: (a) obtaining a blood sample at one time point following an anti-cancer therapy; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference that monitors the response to cancer treatment.

In an embodiment of the present disclosure, there is provided an in-vitro method for monitoring response to cancer treatment, said method comprising: (a) obtaining a blood sample at one time point following an anti-cancer therapy; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference that monitors the response to cancer treatment, wherein the reference is at least one selected from a group consisting of: (i) a blood sample obtained prior to administration of anti-cancer therapy; (ii) a blood sample obtained at a previous time point as compared to the time point mentioned in step (a); (iii) a blood sample obtained at a subsequent time point as compared to the time point mentioned in step (a); and (iv) a blood sample obtained from a cancer-free subject. In another embodiment of the present disclosure, the reference is a blood sample obtained prior to administration of anti-cancer therapy. In yet another embodiment, the reference is a blood sample obtained at a previous time point as compared to the time point mentioned in step (a). In an alternate embodiment, the reference is a blood sample obtained from a cancer-free subject. In another alternate embodiment, the reference is a blood sample obtained at a subsequent time point as compared to the time point mentioned in step (a).

In an embodiment of the present disclosure, there is provided an in-vitro method for monitoring response to cancer treatment, said method comprising: (a) obtaining a blood sample at one time point following an anti-cancer therapy; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference that monitors the response to cancer treatment, wherein a decrease in the expression level of the at least one biomarker of pluripotent stem cell as compared to a reference level indicates a positive response to the cancer treatment, and wherein the reference is at least one selected from a group consisting of: (i) a blood sample obtained prior to administration of anti-cancer therapy; (ii) a blood sample obtained at a previous time point as compared to the time point mentioned in step (a); and (iii) a blood sample obtained from a cancer-free subject. In another embodiment of the present disclosure, the reference is a blood sample obtained prior to administration of anti-cancer therapy. In yet another embodiment, the reference is a blood sample obtained at a previous time point as compared to the time point mentioned in step (a). In an alternate embodiment, the reference is a blood sample obtained from a cancer-free subject.

In an embodiment of the present disclosure, there is provided an in-vitro method for monitoring response to cancer treatment, said method comprising: (a) obtaining a blood sample at one time point following an anti-cancer therapy; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference that monitors the response to cancer treatment, wherein a decrease in the expression level of the at least one biomarker of pluripotent stem cell as compared to a reference level indicates a positive response to the cancer treatment, and wherein the reference is at least one selected from a group consisting of: (i) a blood sample obtained prior to administration of anti-cancer therapy; (ii) a blood sample obtained at a previous time point as compared to the time point mentioned in step (a); and (iii) a blood sample obtained from a cancer-free subject, and wherein the decrease in the expression level is at least 2 folds as compared to the reference level. In another embodiment, the decrease in the expression level is at least 3 folds as compared to the reference level. In yet another embodiment, the decrease in the expression level is at least 4 folds as compared to the reference level. In an alternate embodiment, the decrease in the expression level is at least 5 folds as compared to the reference level.

In an embodiment of the present disclosure, there is provided an in-vitro method for monitoring response to cancer treatment, said method comprising: (a) obtaining a blood sample at one time point following an anti-cancer therapy; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; and (e) comparing the expression level of the at least one biomarker of pluripotent stem cell with an expression level of the at least one biomarker of pluripotent stem cell in a reference that monitors the response to cancer treatment, wherein an increase in the expression level of the at least one biomarker of pluripotent stem cell as compared to a reference level indicates a negative response to the cancer treatment, and wherein the reference is at least one selected from a group consisting of: (i) a blood sample obtained prior to administration of anti-cancer therapy; (ii) a blood sample obtained at a previous time point as compared to the time point mentioned in step (a); and (iii) a blood sample obtained from a cancer-free subject.

In an embodiment of the present disclosure, there is provided an in-vitro method for monitoring response to cancer treatment as described herein, wherein the at least one biomarker of pluripotent stem cell is selected from a group consisting of Oct-4, Sox-2, Nanog, p53, Sirt-1, Sirt-6, Sirt-3, NAD, RAS, ERC, erbB-2, ABL, subsets thereof, and combinations thereof. In another embodiment, the at least one biomarker of pluripotent stem cell is Oct-4. In yet another embodiment, the at least one biomarker of pluripotent stem cell is Oct-4a. In still another embodiment, the at least one biomarker of pluripotent stem cell is Oct-4b.

In an embodiment of the present disclosure, there is provided an in-vitro method for monitoring response to cancer treatment as described herein, wherein the at least one biomarker of pluripotent stem cell is selected from a group consisting of Oct-4, Sox-2, Nanog, p53, Sirt-1, Sirt-6, Sirt-3, subsets thereof, and combinations thereof. In another embodiment, the at least one biomarker of pluripotent stem cell is Sox-2, subsets thereof. In yet another embodiment, the at least one biomarker of pluripotent stem cell is Nanog, subsets thereof. In still another embodiment, the at least one biomarker of pluripotent stem cell is p53, subsets thereof. In an alternate embodiment, the at least one biomarker of pluripotent stem cell is Sirt-1, subsets thereof. In one another embodiment, the at least one biomarker of pluripotent stem cell is Sirt-6, subsets thereof. In one another embodiment, the at least one biomarker of pluripotent stem cell is Sirt-3, subsets thereof.

In an embodiment of the present disclosure, there is provided an in-vitro method for monitoring response to cancer treatment as described herein, wherein the at least one biomarker of pluripotent stem cell is selected from a group consisting of NAD, RAS, ERC, erbB-2, ABL, subsets thereof, and combinations thereof. In another embodiment, the at least one biomarker of pluripotent stem cell is NAD, subsets thereof. In yet another embodiment, the at least one biomarker of pluripotent stem cell is RAS, subsets thereof. In still another embodiment, the at least one biomarker of pluripotent stem cell is ERC, subsets thereof. In an alternate embodiment, the at least one biomarker of pluripotent stem cell is erbB-2, subsets thereof. In a second alternate embodiment, the at least one biomarker of pluripotent stem cell is ABL, subsets thereof.

In an embodiment of the present disclosure, there is provided an in-vitro method for monitoring response to cancer treatment as described herein, wherein obtaining the nucleic acid from the mixture is by any one method selected from a group consisting of: (a) guanidinium thiocyanate-phenol-chloroform nucleic acid extraction; (b) cesium chloride gradient centrifugation method; (c) cetyltrimethylammonium bromide nucleic acid extraction; (d) alkaline extraction; (e) resin-based extraction; and (f) solid phase nucleic acid extraction.

In an embodiment of the present disclosure, there is provided an in-vitro method for monitoring response to cancer treatment as described herein, wherein performing an assay with the nucleic acid for analysing the expression of the at least one biomarker is done by a technique selected from a group consisting of: quantitative PCR, flow cytometry, and Next Generation Sequencing (NGS).

In an embodiment of the present disclosure, there is provided an in-vitro method for monitoring response to cancer treatment as described herein, wherein the control is the expression level of the at least one biomarker of pluripotent stem cells obtained from a cancer-free subject.

In an embodiment of the present disclosure, there is provided an in-vitro method for monitoring response to cancer treatment as described herein, wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; and (iii) processing the second mixture to obtain enriched pluripotent stem cells. In another embodiment, the at least one salt solution is sodium chloride, and the neutral buffer is Ficoll-Hyaque solution.

In an embodiment of the present disclosure, there is provided an in-vitro method for monitoring response to cancer treatment as described herein, wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; and (iii) processing the second mixture to obtain enriched pluripotent stem cells, and wherein the processing of the second mixture comprises, at least one method selected from a group consisting of: (a) extraction process; (b) washing process; (c) centrifugation process, and combinations thereof.

In an embodiment of the present disclosure, there is provided an in-vitro method for monitoring response to cancer treatment as described herein, wherein the method is independent of invasive techniques.

In an embodiment of the present disclosure, there is provided an in-vitro method for detecting a positive response to cancer treatment, said method comprising: (a) obtaining a blood sample-I before administration of an anti-cancer therapy; (b) obtaining a blood sample-II after administration of the anti-cancer therapy; (c) enriching pluripotent stem cells from the blood sample-I to obtain a mixture-I comprising said pluripotent stem cells; (d) enriching pluripotent stem cells from the blood sample-II to obtain a mixture-II comprising said pluripotent stem cells; (e) obtaining nucleic acid-I from the mixture-I; (f) obtaining nucleic acid-II from the mixture-II; (g) independently performing an assay with the nucleic acid-I and the nucleic acid-II for analysing expression level of at least one biomarker of pluripotent stem cell; and (h) comparing the expression level of the at least one biomarker of pluripotent stem cell in the nucleic acid-II with the expression level of the at least one biomarker of pluripotent stem cell in the nucleic acid-I, wherein a decrease in the expression level of the at least one biomarker of pluripotent stem cell in the nucleic acid-II as compared to the expression level of the at least one biomarker of pluripotent stem cell in the nucleic acid-I detects a positive response to the cancer treatment.

In an embodiment of the present disclosure, there is provided an in-vitro method for detecting a positive response to cancer treatment as described herein, wherein the decrease in the expression level of the at least one biomarker of pluripotent stem cell in the nucleic acid-II as compared to the expression level of the at least one biomarker of pluripotent stem cell in the nucleic acid-I is at least 2 folds. In another embodiment, the decrease is at least 3 folds. In another embodiment, the decrease is at least 4 folds. In another embodiment, the decrease is at least 5 folds.

In an embodiment of the present disclosure, there is provided an in-vitro method for detecting a positive response to cancer treatment as described herein, wherein the at least one biomarker of pluripotent stem cell is selected from a group consisting of Oct-4, Sox-2, Nanog, p53, Sirt-1, Sirt-6, Sirt-3, NAD, RAS, ERC, erbB-2, ABL, subsets thereof, and combinations thereof. In another embodiment, the at least one biomarker of pluripotent stem cell is Oct-4. In yet another embodiment, the at least one biomarker of pluripotent stem cell is Oct-4a. In still another embodiment, the at least one biomarker of pluripotent stem cell is Oct-4b.

In an embodiment of the present disclosure, there is provided an in-vitro method for detecting a positive response to cancer treatment as described herein, wherein the at least one biomarker of pluripotent stem cell is selected from a group consisting of Oct-4, Sox-2, Nanog, p53, Sirt-1, Sirt-6, Sirt-3, subsets thereof, and combinations thereof. In another embodiment, the at least one biomarker of pluripotent stem cell is Sox-2, and subsets thereof. In yet another embodiment, the at least one biomarker of pluripotent stem cell is Nanog, and subsets thereof. In still another embodiment, the at least one biomarker of pluripotent stem cell is p53, and subsets thereof. In one alternate embodiment, the at least one biomarker of pluripotent stem cell is Sirt-1, and subsets thereof. In another alternate embodiment, the at least one biomarker of pluripotent stem cell is Sirt-6, and subsets thereof. In yet another alternate embodiment, the at least one biomarker of pluripotent stem cell is Sirt-3, and subsets thereof.

In an embodiment of the present disclosure, there is provided an in-vitro method for detecting a positive response to cancer treatment as described herein, wherein the at least one biomarker of pluripotent stem cell is selected from a group consisting of NAD, RAS, ERC, erbB-2, ABL, subsets thereof, and combinations thereof. In another embodiment, the at least one biomarker of pluripotent stem cell is NAD, and subsets thereof. In yet another embodiment, the at least one biomarker of pluripotent stem cell is RAS, and subsets thereof. In still another embodiment, the at least one biomarker of pluripotent stem cell is ERC, and subsets thereof. In one alternate embodiment, the at least one biomarker of pluripotent stem cell is erbB-2, and subsets thereof. In another alternate embodiment, the at least one biomarker of pluripotent stem cell is ABL, and subsets thereof.

In an embodiment of the present disclosure, there is provided an in-vitro method for detecting a positive response to cancer treatment as described herein, wherein obtaining the nucleic acid from the mixture is by any one method selected from a group consisting of: (a) guanidinium thiocyanate-phenol-chloroform nucleic acid extraction; (b) cesium chloride gradient centrifugation method; (c) cetyltrimethylammonium bromide nucleic acid extraction; (d) alkaline extraction; (e) resin-based extraction; and (f) solid phase nucleic acid extraction.

In an embodiment of the present disclosure, there is provided an in-vitro method for detecting a positive response to cancer treatment as described herein, wherein performing an assay with the nucleic acid for analysing the expression of the at least one biomarker is done by a technique selected from a group consisting of: quantitative PCR, flow cytometry, and Next Generation Sequencing (NGS).

In an embodiment of the present disclosure, there is provided an in-vitro method for detecting a positive response to cancer treatment as described herein, wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; and (iii) processing the second mixture to obtain enriched pluripotent stem cells. In another embodiment, the at least one salt solution is sodium chloride, and the neutral buffer is Ficoll-hyaque solution.

In an embodiment of the present disclosure, there is provided an in-vitro method for detecting a positive response to cancer treatment as described herein, wherein the enriching of the pluripotent stem cells from the blood sample comprises: (i) contacting the blood sample with a neutral buffer in a ratio range of 1:1 to 1:20, to obtain a first mixture; (ii) contacting at least one salt solution to the first mixture in a ratio range of 1:2 to 1:10, to obtain a second mixture; and (iii) processing the second mixture to obtain enriched pluripotent stem cells, and wherein the processing of the second mixture comprises, at least one method selected from a group consisting of: (a) extraction process; (b) washing process; (c) centrifugation process, and combinations thereof.

In an embodiment of the present disclosure, there is provided an in-vitro method for detecting a positive response to cancer treatment as described herein, wherein the method is independent of invasive techniques.

In an embodiment of the present disclosure, there is provided a use of pluripotent stem cell biomarker selected from a group consisting of Oct-4, Sox-2, Nanog, p53, NFκB, Sirt-1, Sirt-6, NAD, RAS, ERC, erbB-2, ABL, subsets thereof, and combinations thereof, for detecting cancer from a blood sample.

In an embodiment of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for detecting cancer from a blood sample, wherein the blood sample is processed using a method comprising: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain a processed second mixture comprising pluripotent stem cells, and wherein the pluripotent stem cell marker is analysed from the processed second mixture obtained from the blood sample.

In an embodiment of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for predicting cancer from a blood sample.

In an embodiment of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for predicting cancer from a blood sample, wherein the blood sample is processed using a method comprising: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain a processed second mixture comprising pluripotent stem cells, and wherein the pluripotent stem cell marker is analysed from the processed second mixture obtained from the blood sample.

In an embodiment of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for grading stage of cancer from a blood sample.

In an embodiment of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for grading stage of cancer from a blood sample, wherein the blood sample is processed using a method comprising: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain a processed second mixture comprising pluripotent stem cells, and wherein the pluripotent stem cell marker is analysed from the processed second mixture obtained from the blood sample.

In an embodiment of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for monitoring progression of anti-cancer therapy from a blood sample.

In an embodiment of the present disclosure, there is provided a use of pluripotent stem cell biomarker selected from a group consisting of Oct-4, Sox-2, Nanog, p53, NFκB, Sirt-1, Sirt-6, Sirt-3, NAD, RAS, ERC, erbB-2, ABL, subsets thereof, and combinations thereof, for monitoring progression of anti-cancer therapy from a blood sample, wherein the blood sample is processed using a method comprising: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain a processed second mixture comprising pluripotent stem cells, and wherein the pluripotent stem cell marker is analysed from the processed second mixture obtained from the blood sample.

In an embodiment of the present disclosure, there is provided a method for treating cancer, said method comprising: (a) obtaining a blood sample from a subject; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; (e) comparing the expression level of the at least one biomarker of pluripotent stem cell with a control, wherein an increase in the expression level of the at least one biomarker as compared to the control detects cancer; and (f) administering anti-cancer therapy to the subject for treating cancer.

In an embodiment of the present disclosure, there is provided a method for treating cancer, said method comprising: (a) obtaining a blood sample from a subject; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; (e) comparing the expression level of the at least one biomarker of pluripotent stem cell with a control, wherein an increase in the expression level of the at least one biomarker as compared to the control detects cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed; and (g) administering anti-cancer therapy to the subject for treating cancer.

In an embodiment of the present disclosure, there is provided a method for treating cancer, said method comprising: (a) obtaining a blood sample from a subject; (b) enriching pluripotent stem cells from the blood sample, to obtain a mixture comprising said pluripotent stem cells; (c) obtaining nucleic acid from the mixture of step (b); (d) performing an assay with the nucleic acid for analysing expression level of at least one biomarker of pluripotent stem cell; (e) comparing the expression level of the at least one biomarker of pluripotent stem cell with a control, wherein an increase in the expression level of the at least one biomarker as compared to the control detects cancer; (f) performing sequence-based assays on the nucleic acid and analysing for mutation in at least one cancer-related marker, wherein presence of mutation in the at least one cancer-related marker indicates presence of a specific type of cancer based on the cancer-related marker analysed; and (g) administering anti-cancer therapy to the subject for treating cancer, and wherein the at least one biomarker of pluripotent stem cell is selected from a group consisting of Oct-4, Sox-2, Nanog, p53, Sirt-1, Sirt-6, Sirt-3, NAD, RAS, ERC, erbB-2, ABL, subsets thereof, and combinations thereof, and wherein the cancer-related marker refers to any marker related to cancer detection. In another embodiment, the cancer-related marker is at least one selected from a group consisting of ABL1, EVI1, MYC, APC, IL2, TNFAIP3, ABL2, EWSR1, MYCL1, ARHGEF12, JAK2, TP53, AKT1, FEV, MYCN, ATM, MAP2K4, TSC1, AKT2, FGFR1, NCOA4, BCL11B, MDM4, TSC2, ATF1, FGFR1OP, NFKB2, BLM, MEN1, VHL, BCL11A, FGFR2, NRAS, BMPR1A, MLH1, WRN, BCL2, FUS, NTRK1, BRCA1, MSH2, WT1, BCL3, GOLGA5, NUP214, BRCA2, NF1, BCL6, GOPC, PAX8, CARS, NF2, BCR, HMGA1, PDGFB, CBFA2T3, NOTCH1, BRAF, HMGA2, PIK3CA, CDH1, NPM1, CARD11, HRAS, PIM1, CDH11, NR4A3, CBLB, IRF4, PLAG1, CDK6, NUP98, CBLC, JUN, PPARG, CDKN2C, PALB2, CCND1, KIT, PTPN11, CEBPA, PML, CCND2, KRAS, RAF1, CHEK2, PTEN, CCND3, LCK, REL, CREB1, RB1, CDX2, LMO2, RET, CREBBP, RUNX1, CTNNB1, MAF, ROS1, CYLD, SDHB, DDB2, MAFB, SMO, DDX5, SDHD, DDIT3, MAML2, SS18, EXT1, SMARCA4, DDX6, MDM2, TCL1A, EXT2, SMARCB1, DEK, MET, TET2, FBXW7, SOCS1, EGFR, MITF, TFG, FH, STK11, ELK4, MLL, TLX1, FLT3, SUFU, ERBB2, MPL, TPR, FOXP1, SUZ12, ETV4, MYB, USP6, GPC3, SYK, ETV6, IDH1, TCF3, and combinations thereof.

In an embodiment of the present disclosure, there is provided a method for treating cancer as described herein, wherein the cancer treated is an early onset of cancer which is not detectable by conventional methods, and thereby, not treatable by conventional anti-cancer therapy. The method of treating as described herein does not involve any invasive techniques like biopsy.

In an embodiment of the present disclosure, there is provided a method for treating cancer as described herein, wherein obtaining the nucleic acid from the mixture is by any one method selected from a group consisting of: (a) guanidinium thiocyanate-phenol-chloroform nucleic acid extraction; (b) cesium chloride gradient centrifugation method; (c) cetyltrimethylammonium bromide nucleic acid extraction; (d) alkaline extraction; (e) resin-based extraction; and (f) solid phase nucleic acid extraction.

In an embodiment of the present disclosure, there is provided a method for treating cancer as described herein, wherein performing an assay with the nucleic acid for analysing the expression of the at least one biomarker is done by a technique selected from a group consisting of: quantitative PCR, flow cytometry, and Next Generation Sequencing (NGS).

In an embodiment of the present disclosure, there is provided a method for treating cancer as described herein, wherein the control is the expression level of the at least one biomarker of pluripotent stem cells obtained from a cancer-free subject.

In an embodiment of the present disclosure, there is provided a method for treating cancer as described herein, wherein the enriching of the pluripotent stem cells from the blood sample comprises: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain enriched pluripotent stem cells.

In an embodiment of the present disclosure, there is provided a method for treating cancer as described herein, wherein the enriching of the pluripotent stem cells from the blood sample comprises: (a) contacting the blood sample with a neutral buffer in a ratio range of 1:1 to 1:20, to obtain a first mixture; (b) contacting at least one salt solution to the first mixture in a ratio range of 1:2 to 1:10, to obtain a second mixture; and (c) processing the second mixture to obtain enriched pluripotent stem cells, and wherein the processing of the second mixture comprises, at least one method selected from a group consisting of: (a) extraction process; (b) washing process; (c) centrifugation process, and combinations thereof.

In an embodiment of the present disclosure, there is provided a method for treating cancer as described herein, wherein the increase in the expression level of the at least one biomarker of pluripotent stem cell is at least 2 folds as compared to the control. In another embodiment, the increase in the expression level of the at least one biomarker of pluripotent stem cell is at least 3 folds as compared to the control. In yet another embodiment, the increase in the expression level of the at least one biomarker of pluripotent stem cell is at least 5 folds as compared to the control. In an alternate embodiment, the increase in the expression level of the at least one biomarker of pluripotent stem cell is 2 folds, or 3 folds, or 4 folds, or 5 folds, or 6 folds, or 7 folds, or 8 folds, or 9 folds, or 10 folds.

In an embodiment of the present disclosure, there is provided a method for treating cancer as described herein, wherein the increase in the expression level of the at least one biomarker of pluripotent stem cell is in a range of 10-20 folds as compared to the control. In another embodiment, the increase in the expression level of the at least one biomarker of pluripotent stem cell is in a range of 20-30 folds as compared to the control. In yet another embodiment, the increase in the expression level of the at least one biomarker of pluripotent stem cell is in a range of 30-40 folds as compared to the control. In one another embodiment, the increase in the expression level of the at least one biomarker of pluripotent stem cell is 40 folds or higher as compared to the control.

In an embodiment of the present disclosure, there is provided a method for treating cancer, said method comprising: (a) obtaining a blood sample from a subject at one time-point following an anti-cancer therapy; (b) enriching pluripotent stem cells from the blood sample to obtain a mixture comprising said pluripotent stem cells; (c) obtaining nucleic acid from the mixture; (d) performing an assay with the nucleic acid for analysing expression level of at least one biomarker of pluripotent stem cell; (e) comparing the expression level of the at least one biomarker of pluripotent stem cell with an expression level of the at least one biomarker of pluripotent stem cell in a reference that monitors the response to anti-cancer therapy, wherein an increase in the expression level of the at least one biomarker of pluripotent stem cell as compared to the reference indicates a negative response to the anti-cancer therapy; and (f) administering an alternate anti-cancer therapy for treating cancer, wherein administering the alternate anti-cancer therapy treats the cancer, and wherein the reference is at least one selected from a group consisting of: (i) a blood sample obtained prior to administration of anti-cancer therapy; (ii) a blood sample obtained at a previous time point as compared to the time point mentioned in step (a); and (iii) a blood sample obtained from a cancer-free subject.

In an embodiment of the present disclosure, there is provided an in-vitro method for detecting cancer as described herein, wherein performing assay with the nucleic acid for evaluating expression of at least one biomarker of pluripotent stem cell is done by employing lateral flow assays.

In an embodiment of the present disclosure, there is provided an in-vitro method for detecting cancer as described herein, wherein performing assay with the nucleic acid for evaluating expression of at least one biomarker of pluripotent stem cell is done using a chip-based assay.

In an embodiment of the present disclosure, there is provided an in-vitro method for detecting cancer as described herein, wherein the method is optimized to be carried out in a chip-based assay.

In an embodiment of the present disclosure, there is provided an in-vitro method for predicting cancer as described herein, wherein performing assay with the nucleic acid for evaluating expression of at least one biomarker of pluripotent stem cell is done by employing lateral flow assays.

In an embodiment of the present disclosure, there is provided an in-vitro method for predicting cancer as described herein, wherein performing assay with the nucleic acid for evaluating expression of at least one biomarker of pluripotent stem cell is done using a chip-based assay.

In an embodiment of the present disclosure, there is provided an in-vitro method for predicting cancer as described herein, wherein the method is optimized to be carried out in a chip-based assay.

In an embodiment of the present disclosure, there is provided an in-vitro method for detecting metabolically altered cells as described herein, wherein performing assay with the nucleic acid for evaluating expression of at least one biomarker of pluripotent stem cell is done by employing lateral flow assays.

In an embodiment of the present disclosure, there is provided an in-vitro method for detecting metabolically altered cells as described herein, wherein performing assay with the nucleic acid for evaluating expression of at least one biomarker of pluripotent stem cell is done using a chip-based assay.

In an embodiment of the present disclosure, there is provided an in-vitro method for detecting metabolically altered cells as described herein, wherein the method is optimized to be carried out in a chip-based assay.

In an embodiment of the present disclosure, there is provided an in-vitro method for detecting quiescent cells as described herein, wherein performing assay with the nucleic acid for evaluating expression of at least one biomarker of pluripotent stem cell is done by employing lateral flow assays.

In an embodiment of the present disclosure, there is provided an in-vitro method for detecting quiescent cells as described herein, wherein performing assay with the nucleic acid for evaluating expression of at least one biomarker of pluripotent stem cell is done using a chip-based assay.

In an embodiment of the present disclosure, there is provided an in-vitro method for detecting quiescent cells as described herein, wherein the method is optimized to be carried out in a chip-based assay.

In an embodiment of the present disclosure, there is provided a kit optimized with relevant ingredients to carry out the in-vitro method as described in the present disclosure.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with a working example, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may vary.

The paragraphs below illustrate the example that depict the working of the method as described in the present disclosure.

Example 1

Study Design

The diagnostic human clinical study was registered prospectively with the Indian Council of Medical Research (ICMR)—Clinical Trial Registry of India (CTRI) under the following number: CTRI/2019/01/017166. The study was a double-blind study of blood samples from major centres across India. The study was conducted with 1000 samples, the outcome of the present study revealed that out of the 1000 samples, 500 samples were from healthy subjects.

Example 2

Detailed In-Vitro Method for Studying the Expression of at Least One Biomarker of Pluripotent Stem Cell Blood samples (5-10 ml) were obtained as part of the registered study. The samples were processed with known techniques before extracting nucleic acid from the samples. The processed samples were subjected to a process for enriching pluripotent stem cells followed by expression analysis of at least one biomarker of pluripotent stem cells. The process as enlisted below was used for detecting, predicting, and monitoring of cancer in a subject. The detailed process as applied is mentioned below.

1. Blood samples (test samples) were obtained at one time point as part of the study.
2. The blood sample was contacted with a neutral buffer in a ratio range of 1:1 (blood sample:neutral buffer) to 1:20, to obtain a first mixture.
3. At least one salt solution was contacted with the first mixture in a ratio range of 1:2 (salt solution:first mixture) to 1:10, to obtain a second mixture.
4. The second mixture was processed to obtain a processed second mixture comprising pluripotent stem cells.
5. Nucleic acid was obtained from the pluripotent stem cells by a method well known in the art. For the purposes of the present exemplification, total mRNA was isolated from the pluripotent stem cells by a method well-known in the art.
6. Expression study was performed using the mRNA sample and the expression was studied for at least one biomarker of pluripotent stem cells selected from a group consisting of Oct-4, Sox-2, Nanog, p53, Sirt-1, Sirt-6, NAD, RAS, ERC, erbB-2, ABL, subsets thereof, and combinations thereof, using quantitative PCR methodology. The expression study was performed by methodology well-known in the art. The expression was done either by NGS or by qPCR studies.
7. In case the objective of the study was for detection or prediction purpose, the expression level as obtained from previous step was compared with a control, wherein the control represents the expression level of the at least one biomarker of pluripotent stem cell obtained from a blood sample isolated from a non-cancer subject.
7A. In case the objective of the study was for monitoring of cancer, the expression level obtained was compared with a reference level, wherein the reference level is at least one selected from a group consisting of: (a) a blood sample obtained prior to administration of anticancer therapy; (b) a blood sample obtained at a previous time point as compared to the time point mentioned in first step; (c) a blood sample obtained at a subsequent time point as compared to the time point mentioned in first step; and (d) a blood sample obtained from a cancer-free subject.

Methodologies and reagents used for achieving the above-mentioned method have been described below.

RNA Isolation and Expression Analysis (Steps 5 and 6)

Total RNA was isolated using RNA Plus (MP Biomedicals, Irvine, CA), according to manufacturer's instructions. First-strand cDNA was synthesized using the Revert Aid First strand cDNA synthesis kit (Thermo scientific, UK) according to the manufacturer's instructions. Briefly, 1 µg of total RNA was incubated with 5×Reaction Buffer and reverse transcriptase mix. The reaction was carried out in Applied Biosystems GeneAmp® thermal cycler 9700 (Applied Bio-systems, USA) as per manufacturer's instructions. The expression levels of the gene transcripts were estimated by real-time PCR system ABI 7500 (Applied Bio-systems, USA) using Thermo Scientific Maxima SYBR Green/ROX qPCR Master Mix kit (Thermo scientific, UK). The 18S rRNA was used as housekeeping gene. The amplification conditions were: initial denaturation at 94° C. for 3 min followed by 40 cycles comprising of denaturation at 94° C. for 10 s, annealing for 20 s, and extension at 72° C. for 30 s followed by melt curve analysis. The fluorescence emitted was collected during the extension step of each cycle. The homogeneity of the PCR amplicons was verified by running the products on 2% agarose gels and also by studying the melt curve. All PCR amplifications were carried out in triplicate. Mean Ct values generated in each experiment using the 7500 Manager software (Applied Biosystems, UK) were used to calculate the mRNA expression levels. The fold change was calculated using $\Delta\Delta Ct$ method. The relative expression levels of each gene were compared with baseline levels taken as one. NGS technology was also sued for analysing expression and/or mutation in biomarker or cancer-related biomarker.

Processing of Second Mixture Comprising Pluripotent Stem Cells (Step 4)

The processing of second mixture comprised a combination of extraction process, washing process, and centrifugation processes to obtain a processed second mixture comprising said pluripotent stem cells.

For the purposes of present exemplification, the processing comprises:

1. The second mixture was subjected to centrifugation at a speed in a range of 1000-6000 rpm for a time period in a range of 5-20 minutes, to obtain a supernatant and a pellet.
2. The supernatant was subjected to extracting or pellet was subjected to washing, to obtain a third mixture.
3. The third mixture was subjected to sequential centrifugation for 2-8 rounds with varying speed ranging from 1000-10,000 rpm to obtain a processed mixture comprising said pluripotent stem cells.

Salt Solution (Step 3)

The salt solution that was used in step 3 is sodium chloride. It is understood that any appropriate salt solution can also be used.

Neutral Buffer (Step 2)

The neutral buffer used in step 2 was selected from a group consisting of ficoll hypaque. It is understood that any appropriate neutral buffer can also be used.

Example 3

Analysis of the Expression Level Studied in Example 2

The in-vitro method as described in Example 2 is capable of detecting as well as predicting cancer in a sample. Also, the method is capable of monitoring cancer progression to check whether a subject is providing a positive response to anti-cancer treatment. Further, the method is capable of monitoring the performance of follow-up care once the treatment is over, to check for chances of any relapse of cancer. The different types of analysis which can be based on the method of present disclosure have been provided below.

Analysis of the Comparison of Expression Level:
1. If the increase in expression level of the at least one biomarker of pluripotent stem cells obtained from a test sample as compared to the control was in the range of 5-50 folds, the sample was declared to be cancer-positive.
2. If the increase in expression level of the at least one biomarker of pluripotent stem cells obtained from a test sample as compared to the control was less than 2 folds, the sample was declared to be cancer-negative.

Grading Different Stages of Cancer:

The method as disclosed in the present disclosure can also be used to grade different stages of cancer. In the study carried out, the different stages of cancer were decided as mentioned below.
1. When expression level of the at least one biomarker of pluripotent stem cells obtained from a test sample as compared to the control increased in a range of 6-10 folds—pre-cancerous stage.
2. When expression level of the at least one biomarker of pluripotent stem cells obtained from a test sample as compared to the control increased in a range of 10-20 folds—stage I cancer.
3. When expression level of the at least one biomarker of pluripotent stem cells obtained from a test sample as compared to the control increased in a range of 20-30 folds—stage II cancer.
4. When expression level of the at least one biomarker of pluripotent stem cells obtained from a test sample as compared to the control increased in a range of 30-40 folds—stage III cancer.
5. When expression level of the at least one biomarker of pluripotent stem cells obtained from a test sample as compared to the control increased in a range of 40 folds and higher—stage IV cancer.

The correlation of the fold-increase in the expression of the at least one biomarker of pluripotent stem cell with the outcome of the in-vitro method as disclosed in the present disclosure has been captured in Table 1 below.

TABLE 1

| Fold-increase in expression of the at least one biomarker of pluripotent stem cell or value or HrC range | Analysis | Recommendation |
| --- | --- | --- |
| 0-2 | Healthy and no risk of cancer | Repeat the test after one year as a check-up measure |
| 2-6 | Inflammation present, gene study to be performed for analysing type of disease involved | Repeat in six months |
| 6-10 | Pre-cancerous - High risk of imminent cancer | Repeat in three months |
| 10-20 | Stage-I - Cancer is present in the body | Visit oncologist |
| 20-30 | Stage-II - Cancer is present in the body | Visit oncologist |
| 30-40 | Stage-III - Cancer is present in the body | Visit oncologist |
| 40 and higher | Stage-IV - Cancer is present in the body | Visit oncologist |

The terms "HrC range" or the "range of fold-change" as described in the present disclosure is interchangeably used to refer to a range of fold-change of the at least one biomarker of pluripotent stem cell. The terms "value" or "HrC value" or "fold-change" have been interchangeably used to refer to a particular value within a specific range. The recommendation from the analysis of the expression level of fold-change has been mentioned herewith. The range provided in the table is with reference to the "control" as defined in the present disclosure, or to the "reference" as defined in the present disclosure, as the case may be.

Analysis for Monitoring Cancer Progression:
1. A decrease in the expression level of the at least one biomarker of pluripotent stem cells obtained from a test sample as compared to a reference indicates a positive response towards anti-cancer therapy, wherein the reference is selected from a group consisting of: (a) a blood sample obtained prior to administration of anti-cancer therapy; (b) a blood sample obtained at a previous time point as compared to the time point of test-blood sample; and (c) a blood sample obtained from a cancer-free subject.

2. An increase in the expression level of the at least one biomarker of pluripotent stem cells obtained from a test sample as compared to a reference indicates a negative response towards anti-cancer therapy, wherein the reference is at least one selected from a group consisting of: (a) a blood sample obtained prior to administration of anti-cancer therapy; (b) a blood sample obtained at a previous time point as compared to the time point of test-blood sample; (c) a blood sample obtained at a subsequent time point as compared to the time point of test-blood sample; and (d) a blood sample obtained from a cancer-free subject.

Example 4

Figure 1:
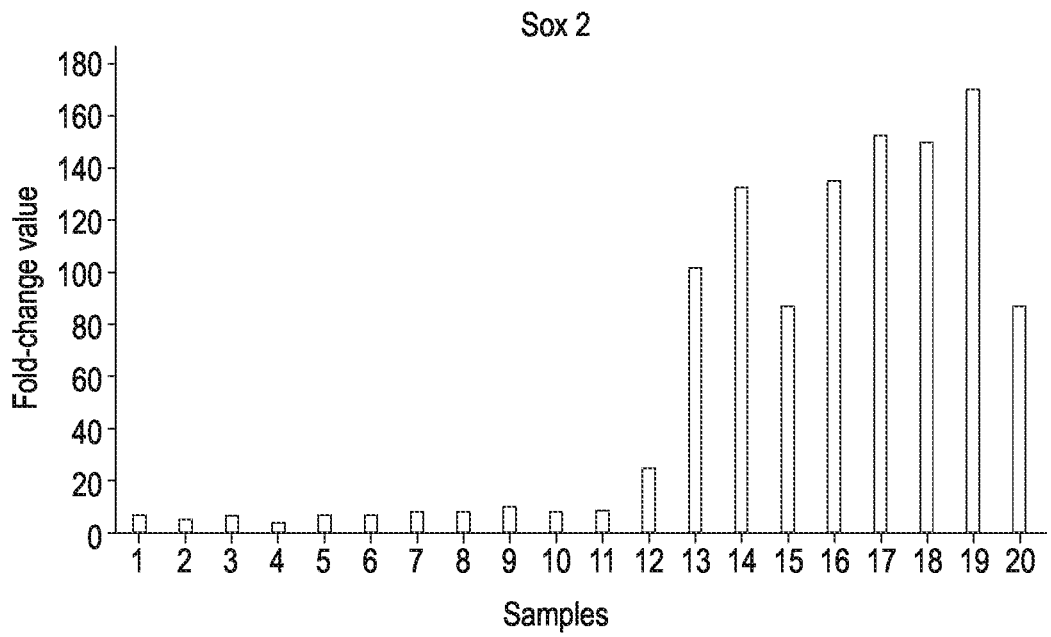
FIG. 1 depicts the fold-change value for Sox 2, obtained with analysing twenty different samples, in accordance with an embodiment of the present disclosure.

Results of the Clinical Study Obtained by Evaluating Expression of Sox 2 Biomarker Among the samples obtained as a part of the present study design, 20 samples were studied for fold-change of expression level of Sox 2 (Gene ID: 6657) from pluripotent cells obtained from respective blood samples. FIG. 1 depicts a graph for fold-change of expression level of Sox 2. It can be observed from FIG. 1 that samples 1 to 11 had the values of fold-change in expression of Sox 2 within 20. Samples 2 and 4 had the values of fold-change of expression less than 6, therefore correlating with the samples free of cancer, whereas all other samples from 1 to 11 had their values correlating with pre-cancerous stage. Samples 13 to 20 had the fold-change of expression higher than 50 folds which, as per the present disclosure, correlates with stage-IV cancer. The observations of the present disclosure correlated with the medical history of the respective samples that were obtained as a part of double-blind study, therefore, proving the ability of the method of present disclosure in detecting presence of cancer.

Example 5

Figure 2:
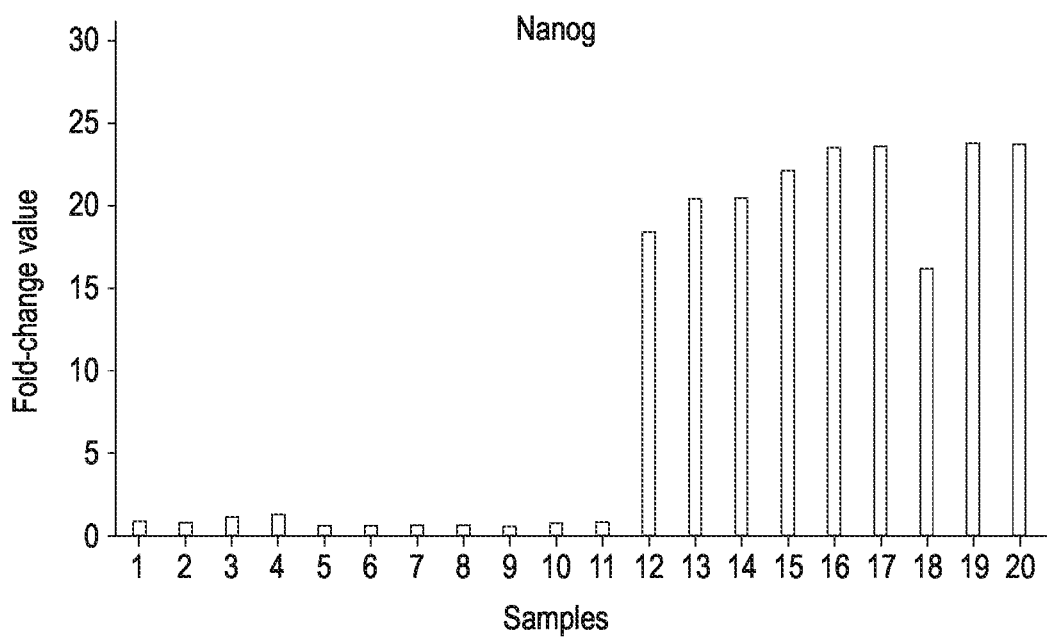
FIG. 2 depicts the fold-change value for Nanog obtained with analysing twenty different samples, in accordance with an embodiment of the present disclosure.

Results of the Clinical Study Obtained by Evaluating Expression of Nanog Biomarker 20 different samples (different from those selected for Example 4) were considered for studying the expression of Nanog (Gene ID: 79923) as a biomarker. FIG. 2 depicts the fold-change in expression of Nanog for 20 samples. It can be observed that samples 1 to 11 had the values of fold-change within 2 which as per the present disclosure correlates with the samples as non-cancer and from cancer-free subjects. Samples 12 and 18 had the values of fold-change in a range of 10-20 folds, therefore correlating stage-I cancer, whereas samples 13-17, 19, and 20 had the values of fold-change in a range of 20-30 folds as compared to a control, therefore, correlating with stage-II cancer. The observations of the present Example correlated with the medical history of the respective samples that were obtained as a part of double-blind study, therefore, proving the ability of the method of present disclosure in detecting presence of cancer.

Example 6

Figure 3:
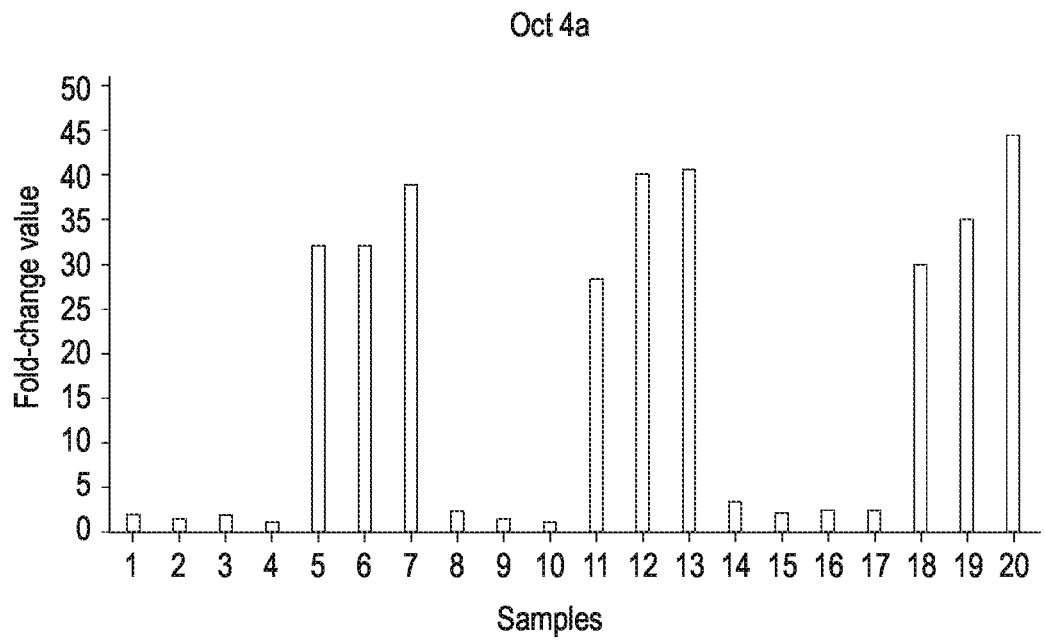
FIG. 3 depicts the fold-change value for Oct-4a obtained with analysing twenty different samples, in accordance with an embodiment of the present disclosure.

Results of the Clinical Study Obtained by Evaluating Expression of Oct-4a Biomarker 20 different samples (different from those mentioned in Examples 4 and 5) were considered for the present example for studying expression of Oct-4a (Gene ID: 642559) as a biomarker. FIG. 3 depicts a graph having fold-change values of the twenty samples. It can be observed that the fold-change value of the sample corroborated with both cancer-free and presence of cancer observations. Samples 1 to 4, 9, 10, 15-17 had the values within 2, thereby, correlating with cancer-free observation, whereas other samples were correlated with either stage-I, stage-II, stage-III, or stage-IV cancer as per the values. The observations of the present Example correlated with the medical history of the respective samples that were obtained as a part of double-blind study, therefore, proving the ability of the method of present disclosure in detecting presence of cancer.

Example 7

Results of the Clinical Study Obtained by Evaluating Expression of Sirt-1 Biomarker 20 different samples (different from those mentioned in Examples 4-6) were considered for the present example for studying expression of Sirt-1 (Gene ID: 23411) as a biomarker.

Figure 4:
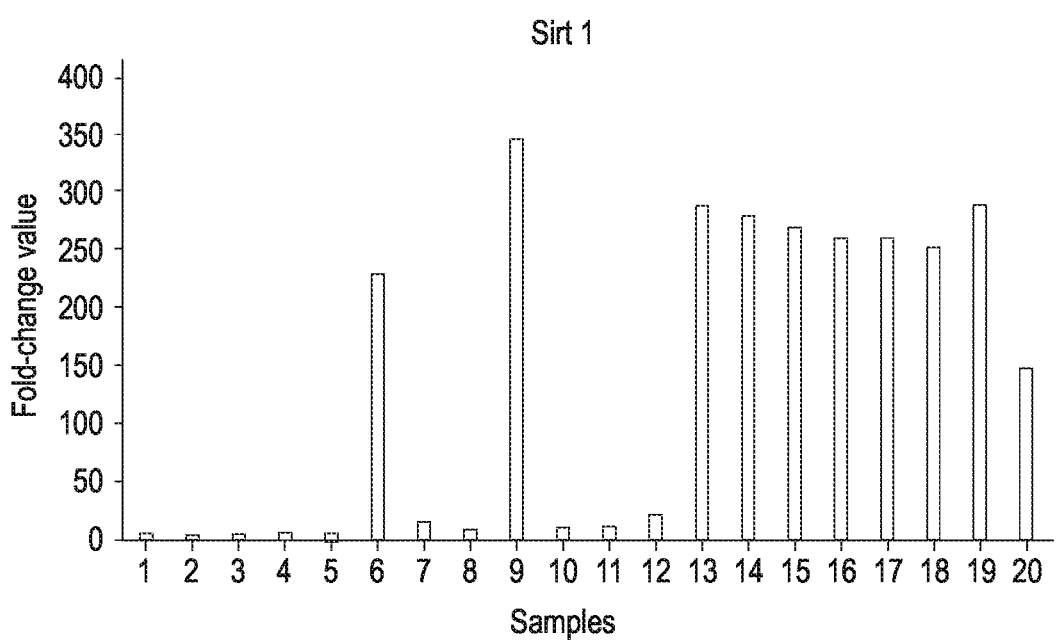
FIG. 4 depicts the fold-change value for Sirt 1 obtained with analysing twenty different samples, in accordance with an embodiment of the present disclosure.

FIG. 4 depicts a graph having fold-change values of the 20 samples. Since, none of the samples had fold-change value lesser than 2 folds, none of the sample correlated with absence of cancer. Samples 6, 9, 13-20 had fold-change values more than 50, thereby, correlating with presence of stage-IV cancer. The observations of the present Example correlated with the medical history of the respective samples that were obtained as a part of double-blind study, therefore, proving the ability of the method of present disclosure in detecting presence of cancer.

Example 8

Results of the Clinical Study Obtained by Evaluating Expression of Sirt 6 Biomarker Among the samples obtained as a part of the present study design, 20 different samples (different from Examples 4-7) were studied for fold-change of expression level of Sirt 6 (Gene ID: 51548) from pluripotent cells obtained from respective blood samples. The method for detecting the presence of cancer was as per the present disclosure and described in Example 2.

Figure 5:
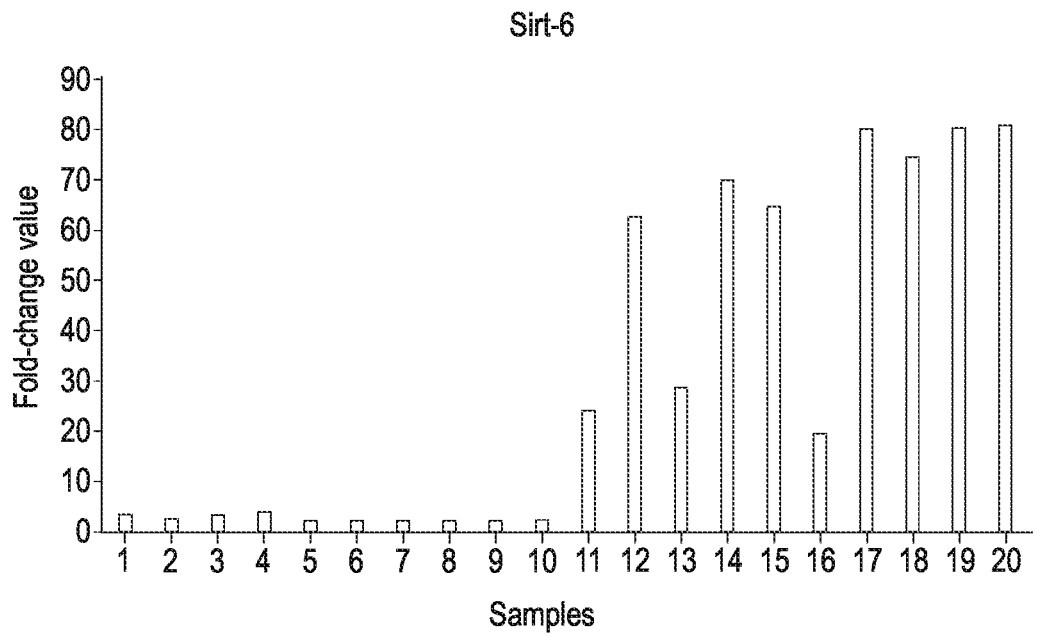
FIG. 5 depicts the fold-change value for Sirt 6 obtained with analysing twenty different samples, in accordance with an embodiment of the present disclosure.

FIG. 5 depicts a graph for fold-change of expression level of Sirt 6. It can be observed from FIG. 5 that samples 5 to 9 had the values of fold-change within 0-2, correlating to healthy sample. Samples 11-20 had their fold-change values within the cancerous range, and were therefore marked as cancer-positive samples. The observations of the present disclosure correlated with the medical history of the respective samples that were obtained as a part of double-blind study, therefore, proving the ability of the method of present disclosure in detecting presence of cancer.

Example 9

Results of the Clinical Study Obtained by Evaluating Expression of NFκB Biomarker Twenty different samples (different from those selected for Examples 4-8) were considered for studying the expression of NFκB (Gene ID: 4791) as a biomarker. The method for detecting the presence of cancer was as per the present disclosure and described in Example 2.

Figure 6:
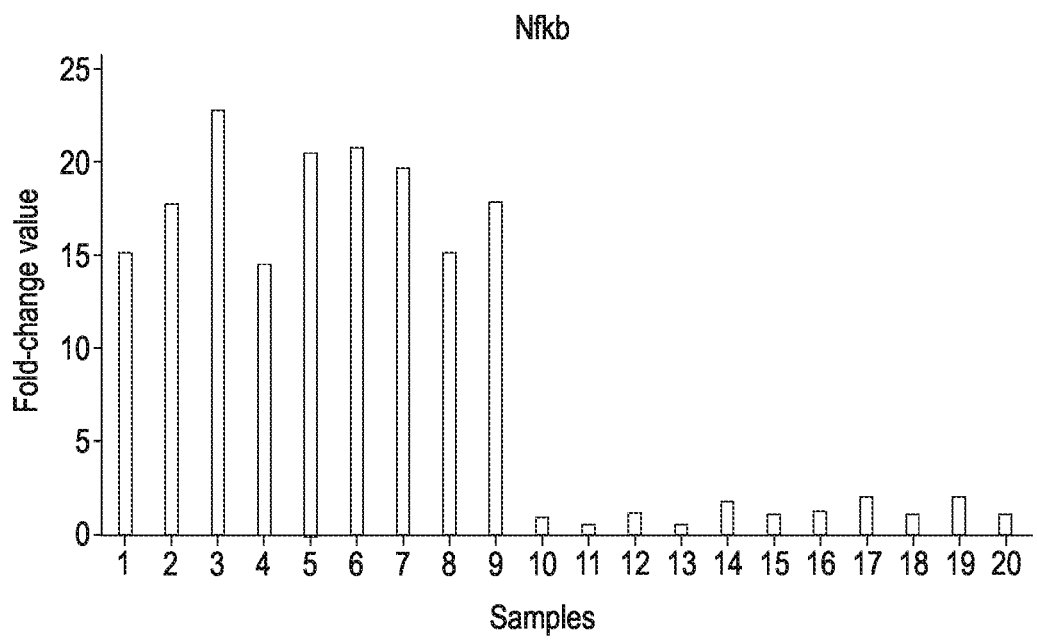
FIG. 6 depicts the fold-change value for NFκB obtained with analysing twenty different samples, in accordance with an embodiment of the present disclosure.

FIG. 6 depicts the fold-change in expression of NFκB for twenty samples. It can be observed that samples 1 to 9 had the values of fold-change within the range specified for stage-I cancer or stage-II cancer. Samples 10 to 20 had the values of fold-change within 2, therefore, correlating with non-cancer reading. The observations of the present Example correlated with the medical history of the respective samples that were obtained as a part of double-blind study, therefore, proving the ability of the method of present disclosure in detecting presence of cancer.

Example 10

Results of the Clinical Study Obtained by Evaluating Expression of Oct-4 Biomarker Twenty different samples (different from those mentioned in Examples 3-8) were considered for the present example for studying expression of Oct-4 (Gene ID: 642559) as a biomarker. The method for detecting the presence of cancer was as per the present disclosure and described in Example 2.

Figure 7:
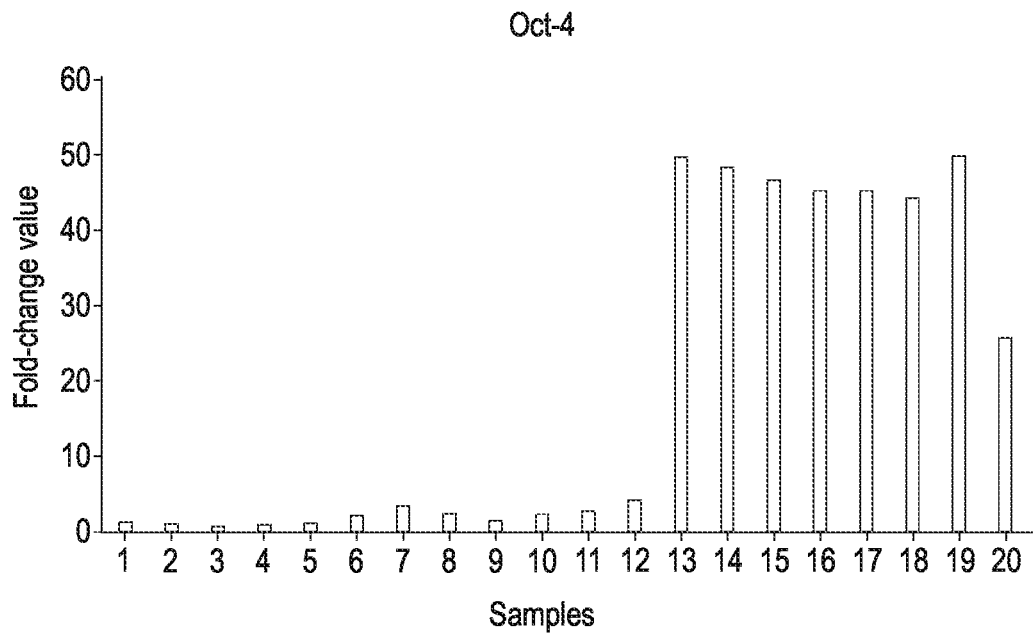
FIG. 7 depicts the fold-change value for Oct-4 obtained with analysing twenty different samples, in accordance with an embodiment of the present disclosure.

FIG. 7 depicts a graph having fold-change values of the 20 samples. It can be observed that samples 1 to 12 had the values of fold-change as compared to the control within 5, thereby, correlating with absence of cancer. Samples 7, 8, 10, and 12 having values of more than 2 were categorised under presence of inflammation and are suspected to have a certain kind of abnormality or a condition leading to inflammation in at least one part of the subject's body. Samples 13-19 which had fold-change values in a range of 40-50 folds correlated with the samples having stage-IV cancer, and sample 20 correlated with presence of stage II cancer as the fold-change value was in a range of 20-30 folds. The observations of the present Example correlated with the medical history of the respective samples that were obtained as a part of double-blind study, therefore, proving the ability of the method of present disclosure in detecting presence of cancer.

Example 11

Results of the Clinical Study Obtained by Evaluating Expression of p53 Biomarker Twenty different samples (different from those mentioned in Examples 4-10) were considered for the present example for studying expression of p53 (Gene ID: 7157) as a biomarker. The method for detecting the presence of cancer was as per the present disclosure and described in Example 2.

Figure 8:
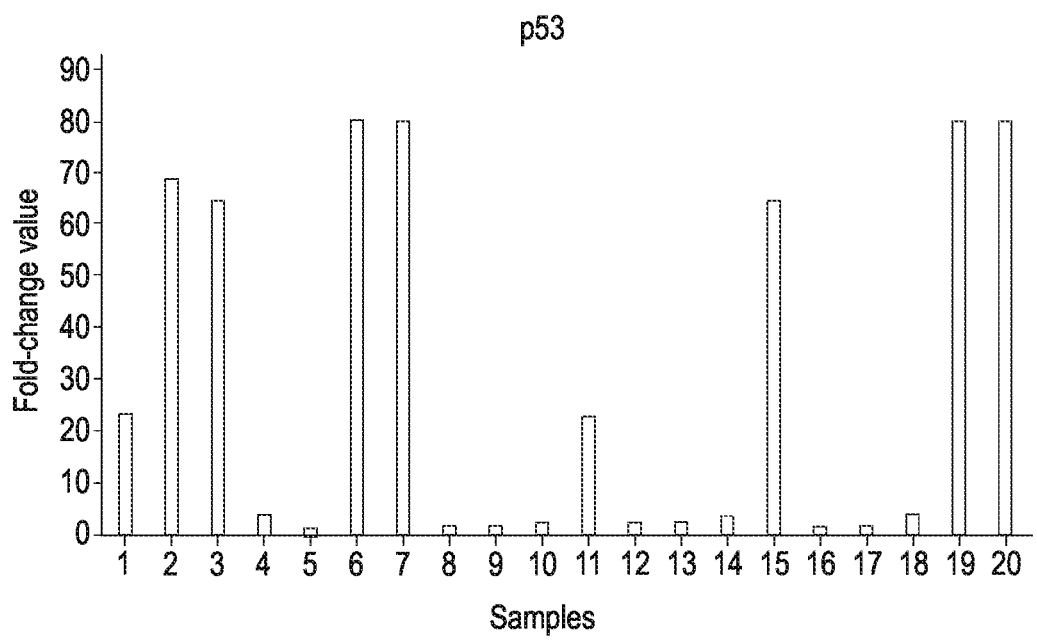
FIG. 8 depicts the fold-change value for p53 obtained with analysing twenty different samples, in accordance with an embodiment of the present disclosure.
Figure 9:
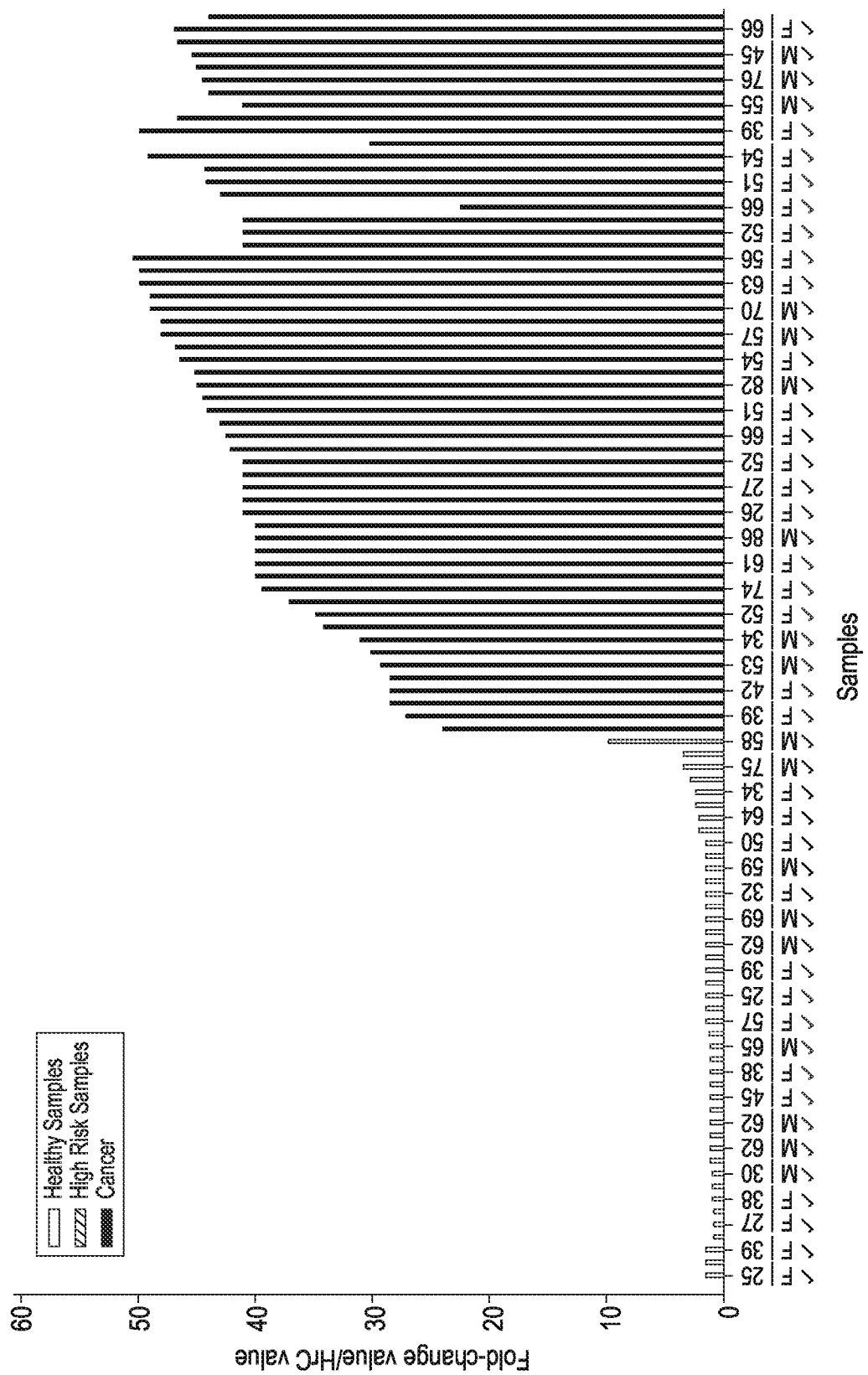
FIG. 9 depicts a representative first graph showing the fold-change value for at least one biomarker of pluripotent stem cell as disclosed in the present study with a cohort of 1000 samples, in accordance with an embodiment of the present disclosure. The tick marks below show concurrence with the actual clinical status by an independent reviewer in the blinded study.

FIG. 8 depicts a graph having fold-change values of the twenty samples. Samples 5, 8, 9, 16, and 17 had the fold-change values within 2, thereby, being cancer-free samples. Samples 2, 3, 6, 7, 15, 19, and 20 had the fold-change values beyond a value of 50, thereby, correlating with advanced stages of cancer (stage-IV). The observations of the present Example correlated with the medical history of the respective samples that were obtained as a part of double-blind study, therefore, proving the ability of the method of present disclosure in detecting presence of cancer.

Example 12

Results of the Entire Samples Collected as a Part of the Present Study Design

The present Example describes the results of a 1000-sample study performed to establish the working of the in-vitro method disclosed in the present disclosure. FIGS. 9 to 18 depict the fold-change (HrC value) in the expression of the at least one biomarker of pluripotent stem cells selected from a group consisting of Oct-4, Sox-2, Nanog, p53, Sirt-1, Sirt-6, Sirt-3, NAD, RAS, ERC, erbB-2, ABL, subsets thereof, and combinations thereof. The method used for arriving at the fold change value was as per the in-vitro method of the present disclosure as described in Example 2. Each of the FIGS. from 9 to 18 depict the data for 100 samples each. The open bars represent samples analysed to be healthy as per the process of present disclosure, the solid bars represent cancer-positive samples, and the cross-hatched bars indicate samples to be falling under the category of high-risk of imminent cancer.

Several case studies were performed as part of evaluating the method of the present disclosure. A few selected case studies are presented herein below as part of the present example. The term "HrC test" refers to the in-vitro process as disclosed in the present disclosure.

Case Study 1

Subject details—A blood sample of a 68-year-old male was received as part of the present study and without knowledge of any other details, the HrC test was conducted on the sample.

The HrC test result on Day 0 showed a reading of 9.78 which indicated that the individual was a high-risk candidate. Besides high-risk category, HrC test also specifically detected that the organ at risk was prostate, due to presence of mutation in hoxb13 gene. At this stage, the circulating tumour cells (CTCs) were absent. The results were shared with the individual and he underwent further analysis which revealed that the prostate specific antigen (PSA) levels were high and the prostate gland was swollen (Day 7). With the oncologists' consultation, the individual underwent biopsy which indicated hoxb13 mutation (Day 45), and the patient underwent prostatectomy (Day 65). On the day of the operation, the HrC value was 10.89, which revealed that the cancer was indeed progressing. On Day 75, the results of gene expression from prostate tissue revealed that the gene expression results and mutation results obtained from HrC test (performed from blood sample) were near identical to the results obtained from the tissue. Therefore, HrC test has the ability to provide the information that a biopsy could provide, and that too at an earlier stage and without using any invasive technique. After 6 weeks (Day 95) of the removal of tumour, the HrC test showed a reading of 2.1, which indicated that the individual was cancer-free.

Advantages conferred by the present disclosure—The present case study provides an evidence that the HrC test was successful in diagnosis and prognosis of cancer. The gene expression and mutation results were near identical in (cancer) tissue and blood. HrC test could detect cancer from only a blood sample even before existence of CTCs.

Medical history—The subject's medical history form disclosed the following details: Acidity, fatty liver and diabetic condition.

Case Study 2

Subject details—A blood sample of a 39-year-old female was received as part of the present study. The subject was diagnosed with cervical adenocarcinoma and had been scheduled to undergo surgery for the removal of the tumour.

On the day of surgery (Day 0), the HrC value was 32.116 and CTC were positive. Ten days post-surgery (Day 10), the HrC value had fallen to 20.142 due to removal of the tumour. Post-surgery, she underwent 6 cycles of adjuvant chemo-therapy (Day 20 to Day 160) and after the completion of the chemo-treatment, the test for CTC was negative along with PET scan showing absence of lesion. As per the imaging technique, the patient was declared cancer-free, but HrC value showed a reading of 6.48 (high-risk category) (Day 167) and the in-vitro method of the present disclosure appropriately detected the patient to be in the high-risk category and at the risk of relapse. Further to the inputs provided by the present study, she is at present undergoing 3 more cycles of chemotherapy.

Advantages conferred by the present disclosure—The HrC test successfully aided oncologists to monitor the disease progression and risk of relapse by a non-invasive technique. Thus, HrC test can detect cancer and risk of relapse prior to the existence of CTC.

Case Study 3

Subject details—A blood sample of a 65-year-old female was received as part of the present study.

Medical history—The subject was diagnosed with a tumour above ovary.

The HrC value was 41.28 (Day 0) and cancer antigen 125 (CA125) was 198.8 along-with pain in the abdomen (Day 3). Post diagnosis, the patient underwent surgery (Day 7) for the removal of both ovaries, uterus, and fallopian tube. The immuno-histochemistry analysis (Day 10) of the removed tissue suggested the primary site of cancer lies in the stomach since the tissue was positive for CK-20, CDX2/SATB2 marker. The doctors were unable to detect primary site of cancer and it was further impacting the course of treatment (Day 30). The HrC test was able to accurately detect the primary site of cancer as the appendix (Day 44).

Advantages conferred by the present disclosure—HrC test was successful in diagnosis of cancer and detection of a primary site of the cancer in cases where the primary site cannot be detected using conventional methods. Therefore, the HrC test helped oncologists to chart a course for treating the cancer in case where the primary site was not getting detected, thereby, increasing the survival chances of the subject.

Summary of the 1000-sample study: The types of cancer that were detected, predicted, monitored, as part of the present study have been summarised in the table below.

TABLE 2

| Type of Cancer | Number |
| --- | --- |
| Breast cancer | 74 |
| Liver cancer | 61 |
| Ovarian cancer | 54 |
| Lung cancer | 49 |
| Leukemia | 39 |
| Prostate cancer | 36 |
| Lymphoma | 32 |
| Pancreatic cancer | 29 |
| Cervical cancer | 24 |
| Colon cancer | 22 |
| Osteosarcoma | 18 |
| Testicular cancer | 16 |

TABLE 2-continued

| Type of Cancer | Number |
| --- | --- |
| Thyroid cancer | 15 |
| Gastric cancer | 13 |
| Ewing Sarcoma | 9 |
| Bladder cancer | 8 |
| Gastrointestinal Stromal Tumor (GIST) | 1 |

As can be inferred by Table 2, as per the availability of the samples, the method disclosed in the present disclosure was able to effectively and accurately detect or predict or monitor a vast array of cancers.

Advantages of the present disclosure—The case studies mentioned in the present example clearly prove that the in-vitro method as disclosed in the present disclosure provides more advantages and is more versatile and comprehensive than the presently used techniques such as, PET, CT, and liquid biopsy. The advantages are listed below.

Detecting cancer—The method as disclosed in the present disclosure is able to detect cancer simply by analysing a blood sample, even before the CTC appear and even before PET or CT scan can work, therefore, increasing the survival chances of patients inflicted with cancer.

Predicting cancer—The method as disclosed in the present disclosure is able to predict the likelihood of manifestation of cancer in a subject simply by analysing a blood sample. The method can accurately predict the type of cancer which can get manifested in a subject, which no technique available at present can do.

Monitoring cancer treatment—The method as disclosed herein monitors progression of cancer in a subject undergoing anti-cancer therapy by a simple blood analysis. The specific advantage conferred by the method of present disclosure is that the method can be performed very frequently as compared to a PET scan which can be performed only once over a span of 6 months, thereby, saving precious time of anti-cancer therapy. The method also checks cancer relapse and is able to guide oncologists as to the requirement of any alternate methods of cancer therapy without wasting time.

Detecting a specific type of cancer without the need to perform a biopsy: The method as disclosed in the present disclosure is able to combine the analysis of expression level of the at least one biomarker of pluripotent stem cell with the mutational studies of the cancer-related marker to accurately detect the specific type of cancer and stage of cancer from a blood sample, thereby, avoiding the use of any invasive techniques like biopsy. Also, since biopsies suffer from a risk of activating cancer-related activities in subject, the method as disclosed in the present disclosure has a specific advantage of not having any such risks involved.

Table 3 below depicts the advantages conferred by the in-vitro method of the present disclosure as compared to well-known techniques like PET scan, CT scan, and traditional blood and tissue biopsy study.

TABLE 3

|  | PET scan | CT scan | Liquid Biopsy | Hrc test (method as disclosed in the present disclosure) |
| --- | --- | --- | --- | --- |
| Technique/Technology | Imaging | Imaging | Traditional Blood (detect CTC) and tissue Biopsy analysis | Advanced blood-based study |
| Location detection | Pinpoint location of the lesions | Pinpoint location of the lesions | No. Location indicates only presence of cancer in the body | Can detect the exact location of the cancer |

TABLE 3-continued

|  | PET scan | CT scan | Liquid Biopsy | Hrc test (method as disclosed in the present disclosure) |
|---|---|---|---|---|
| Activity level detection | Yes, only for visible lesion | No | No | Yes |
| Size | For large lesions | For large lesions | No | Yes. Macro level |
| Detection at the stage of cancer | Stages for solid cancer | Stages for solid cancer | For some cancers and subject to false-negative | All stages, All cancer |
| Frequency | Once in 6-8 months | Once in 6-8 months | Blood test - Unlimited Tissue test - Limited | Unlimited |
| Hazardous | Radiation equals 7000 X rays | Radiation equals 4000 X rays | Blood test - Non-hazardous Biopsy test- Highly Invasive | Non-Hazardous |
| Carcinogenic | Yes | Yes | No | No |
| Cancer Types | Only applies to solid tumour; blood cancer cannot be detected | Only applies to solid tumour; blood cancer cannot be detected | Applies to solid and liquid both but not relevant in many cancer types | All types of cancer can be detected-solid and blood both |
| Detection Strength | Stage 1 A cannot be detected | Stage 1 A cannot be detected | Not detected until shedding begins in Stage 2; History of false negative | Detected all stages including (Pre-cancer-before stage 1) Highly accurate |
| Scope | Diagnostic-Post Manifestation of tumour | Diagnostic-Post Manifestation of tumour | Diagnostic- Post Manifestation of tumour | Diagnostic and Prognostic Pre and Post Manifestation of tumour |
| Average Survival rate | 1-3X | 1-3X | 3-5X | >10X |
| Typical detection | Late Stage | Late Stage | Mid to Late Stage | Early to Pre-Stage |

The present disclosure discloses a simple, efficient, non-hazardous, and sensitive method for detecting, predicting and monitoring cancer and detecting cancer mutations in a subject from a simple blood sample obtained from the subject. The method comprises enrichment of pluripotent stem cells from the blood sample, and analysis of the expression of pluripotent stem cell markers.

A significant advantage of the method as disclosed in the present disclosure is that, without the use of any invasive technique, the method can predict and/or detect cancer in a subject. One other significant advantage is that the method as disclosed herein can analyse mutations in a certain set of genes that can effectively deduce the organ(s) which has been affected by cancer. No other method known in the field can effectively deduce the organ which has been infected by cancer by a simple blood test. The process of the present disclosure effectively deduces the organ where cancer resides from only a blood sample. In conventional methods, a PET scan which involves the use of radioisotope is required to confirm the organ which has been affected. The method involves an assay performed using only a blood sample from the subject as opposed to tissue biopsy that is conventionally done. Since, the method is free of any use of radioactive isotopes, it can be performed frequently on a subject who has been undergoing treatment for cancer. Therefore, it can be even used to check whether treatment being provided is working or not. The method is highly sensitive in a manner that it can predict the possibility of a subject getting diagnosed with cancer in a near future, by using a blood sample from the subject. The method as disclosed in the present disclosure can be used in conjunction with conventional techniques to provide an effective combinatorial procedure for detecting or predicting or monitoring cancer in a subject. The method as disclosed in the present disclosure is applicable for all types of cancer, a non-limiting list has been disclosed in the present disclosure.

We claim:

1. A method for detecting a presence or an absence of cancer in a subject, comprising:

(a) obtaining a whole blood sample from the subject;

(b) contacting the whole blood sample with a neutral buffer and then with a salt solution, followed by performing centrifugation at a speed of between 1000 rotations per minute (rpm) and 6000 rpm, for a time period of between 5 minutes and 20 minutes, to obtain a pellet, wherein the contacting is performed with a first ratio in a range of 1:1 to 1:20 between the whole blood sample and the neutral buffer, and wherein the contacting is performed with a second ratio in a range of 1:2 to 1:10 between (1) the salt solution and (2) the whole blood sample contacted with the neutral buffer;

(c) washing the pellet, and re-suspending cells from the washed pellet in a buffer;

(d) performing centrifugation on the re-suspended cells, to obtain a second pellet of cells;

(e) isolating messenger ribonucleic acid (mRNA) from the second pellet of cells;

(f) assaying the isolated mRNA to (i) detect a presence of Oct-4a-expressing cells among the second pellet of cells and (ii) determine an expression level of Oct-4a;

(g) comparing the determined expression level of Oct-4a with a reference expression level; and (h) detecting the presence or the absence of cancer in the subject based at least in part on whether the determined expression level of Oct-4a is increased by at least 10 folds as compared to the reference expression level.

2. The method of claim 1, further comprising detecting the presence or the absence of cancer in the subject based at least in part on whether the determined expression level of Oct-4a is increased by 10-20 folds as compared to the reference expression level.

3. The method of claim 1, further comprising detecting the presence or the absence of cancer in the subject based at least in part on whether the determined expression level of Oct-4a is increased by 20-30 folds as compared to the reference expression level.

4. The method of claim 1, further comprising detecting the presence or the absence of cancer in the subject based at least in part on whether the determined expression level of Oct-4a is increased by 30-40 folds as compared to the reference expression level.

5. The method of claim 1, further comprising detecting the presence or the absence of cancer in the subject based at least in part on whether the determined expression level of Oct-4a is increased by at least 40 folds as compared to the reference expression level.

6. The method of claim 1, wherein (e) further comprises performing a technique selected from the group consisting of: guanidinium thiocyanate-phenol-chloroform nucleic acid extraction, cesium chloride gradient centrifugation method, cetyltrimethylammonium bromide nucleic acid extraction, alkaline extraction, resin-based extraction, and solid phase nucleic acid extraction.

7. The method of claim 1, wherein the reference expression level is obtained from a cancer-free subject.

8. The method of claim 1, wherein the method does not comprise performing invasive techniques on the subject.

9. The method of claim 1, wherein (f) further comprises performing quantitative polymerase chain reaction (qPCR), flow cytometry, or transcriptome sequencing.

10. The method of claim 9, wherein (f) further comprises performing the qPCR.

11. The method of claim 9, wherein (f) further comprises performing the transcriptome sequencing.

12. The method of claim 1, wherein (h) further comprises detecting the presence of cancer in the subject, and wherein the method further comprises determining a stage of the cancer in the subject.

13. The method of claim 1, wherein (h) further comprises detecting the presence of cancer in the subject, and wherein the method further comprises determining an effect of an anti-cancer therapy on the cancer in the subject.

14. The method of claim 1, wherein (h) further comprises detecting the presence of cancer in the subject, and wherein the method further comprises monitoring a progression or regression of the cancer in the subject.

15. The method of claim 1, wherein (h) further comprises detecting the presence of cancer in the subject, and wherein the method further comprises determining a risk of relapse of the cancer in the subject.

16. The method of claim 1, wherein the neutral buffer comprises a Ficoll hypaque solution.

17. The method of claim 9, wherein (f) further comprises performing the flow cytometry.

18. The method of claim 1, wherein (h) further comprises detecting the presence of cancer in the subject, when the determined expression level of Oct-4a is increased by at least 10 folds as compared to the reference expression level.

* * * * *